(12) United States Patent
Grote et al.

(10) Patent No.: US 8,946,419 B2
(45) Date of Patent: Feb. 3, 2015

(54) (+)-6-HYDROXY-MORPHINAN OR (+)-6-AMINO-MORPHINAN DERIVATIVES

(71) Applicant: Mallinckrodt LLC, Hazelwood, MO (US)

(72) Inventors: Christopher W. Grote, Webster Groves, MO (US); Amruta R. Poreddy, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 14/045,009

(22) Filed: Oct. 3, 2013

(65) Prior Publication Data

US 2014/0031543 A1     Jan. 30, 2014

Related U.S. Application Data

(63) Continuation-in-part of application No. 12/710,390, filed on Feb. 23, 2010, now Pat. No. 8,563,724.

(60) Provisional application No. 61/145,449, filed on Feb. 23, 2009.

(51) Int. Cl.
C07D 489/00     (2006.01)
C07D 489/08     (2006.01)

(52) U.S. Cl.
CPC .................................. C07D 489/08 (2013.01)
USPC ......................................................... 546/44

(58) Field of Classification Search
CPC .................................................... C07D 489/08
USPC .......................................................... 546/44
See application file for complete search history.

(56) References Cited

U.S. PATENT DOCUMENTS

| | | | |
|---|---|---|---|
| 2,578,787 A | 12/1951 | DeBenneville |
| 2,772,270 A | 11/1956 | Weiss |
| 3,717,643 A | 2/1973 | Archer |
| 4,089,855 A | 5/1978 | Chatterjie et al. |
| 4,443,605 A | 4/1984 | Kotick et al. |
| 4,521,601 A | 6/1985 | Rice |
| 4,673,679 A | 6/1987 | Aungst et al. |
| 4,775,759 A | 10/1988 | Rice et al. |
| 4,795,813 A | 1/1989 | Schwartz |
| 4,912,114 A | 3/1990 | Revesz |
| 4,991,391 A | 2/1991 | Kosinski |
| 5,240,933 A | 8/1993 | Merz et al. |
| 5,336,483 A | 8/1994 | de Costa et al. |
| 5,668,285 A | 9/1997 | Rice et al. |
| 5,693,820 A | 12/1997 | Helmchen et al. |
| 5,739,145 A | 4/1998 | Nagase et al. |
| 5,756,745 A | 5/1998 | Kavka |
| 5,847,142 A | 12/1998 | Mudryk et al. |
| 6,174,891 B1 | 1/2001 | Nagase et al. |
| 6,184,381 B1 | 2/2001 | Ikariya et al. |
| 6,277,859 B1 | 8/2001 | Nagase et al. |
| 6,323,212 B1 | 11/2001 | Nagase et al. |
| 6,509,467 B1 | 1/2003 | Blacker et al. |
| 6,887,999 B1 | 5/2005 | Likhotvorik |
| 7,045,646 B2 | 5/2006 | Tanis et al. |
| 7,230,134 B2 | 6/2007 | Borner et al. |
| 2004/0077863 A1 | 4/2004 | Scammells et al. |
| 2004/0204434 A1 | 10/2004 | Shafer et al. |
| 2004/0267051 A1 | 12/2004 | Boerner et al. |
| 2005/0038061 A1 | 2/2005 | Schutz et al. |
| 2005/0182258 A1 | 8/2005 | Schmidhammer et al. |
| 2006/0182692 A1 | 8/2006 | Fishburn et al. |
| 2006/0258696 A1 | 11/2006 | Moss et al. |
| 2007/0265293 A1 | 11/2007 | Boyd et al. |
| 2008/0009629 A1 | 1/2008 | Avdagic |
| 2008/0045715 A1 | 2/2008 | Mitchell et al. |
| 2008/0161570 A1 | 7/2008 | Perez et al. |
| 2008/0176884 A1 | 7/2008 | Perez et al. |
| 2008/0207669 A1 | 8/2008 | Perez et al. |
| 2008/0214817 A1 | 9/2008 | Dlubala |
| 2008/0234306 A1 | 9/2008 | Perez et al. |
| 2008/0234307 A1 | 9/2008 | Schuetz et al. |
| 2008/0274119 A1 | 11/2008 | Moss et al. |
| 2009/0062544 A1 | 3/2009 | Wakita et al. |
| 2010/0022774 A1 | 1/2010 | Kvernenes et al. |
| 2010/0041888 A1 | 2/2010 | Grote et al. |

FOREIGN PATENT DOCUMENTS

| | | |
|---|---|---|
| CH | 683 005 A5 | 12/1993 |
| CN | 1115318 | 1/1996 |
| CN | 1115318 A | 1/1996 |
| DE | 922 827 | 1/1955 |
| DE | 922827 | 1/1955 |
| DE | 1119284 | 12/1961 |
| EP | 0 034 480 | 8/1981 |
| EP | 0418591 | 3/1991 |
| EP | 0 663 401 A1 | 7/1995 |

(Continued)

OTHER PUBLICATIONS

Abdel-Magid et al., "Reductive Animation of Aldehydes and Ketones . . .", Tetrahedron Letters, vol. 31, No. 39, 1990, p. 5395-5598.

Beyerman et al., "Synthesis of racemic and optically active codeine and morphine via the N-formylnordihydrothebainones", Journal of the Royal Netherlands Chemical Society, 97, 5, May 1978, pp. 127-130.

Beyerman et al., "Synthesis of racemic and of ( +)—and ( −)-1 methyldihydrothebainone. (Chemistry of opium alkaloids, Part IV)", Recl. Trav. Chim. Pays-Bas, 1976, 75, p. 184-188.

Bognar et al., "Conversions of Tosyl and Mesyl Derivatives of the Morphine Group. Azido Derivatives of Morphine Alkaloids", Izvestiya po Khimiya, Bulgarian Academy of Sciences, 1975, 81(1), p. 203-215.

Borch et al., "The cyanohydridoborate Anion as a Selective Reducing Agent", Journal of the American Chemical Society, 93:12, Jun. 16, 1971, p. 2897-2904.

Borch et al., "A New Method for the Methylation of Amines", J. Org. Chem., vol. 36, No. 10, 1972, pp. 1673-1674.

(Continued)

*Primary Examiner* — Shawquia Jackson

(57) ABSTRACT

The present invention provides (+)-morphinanium compounds comprising substituted 6-hydroxy or 6-amine groups. The invention also provides methods for inhibiting microglial activation by administering the compounds of the invention.

20 Claims, No Drawings

(56) References Cited

FOREIGN PATENT DOCUMENTS

| | | |
|---|---|---|
| EP | 0 879 823 | 11/1998 |
| JP | 41-6905 | 4/1966 |
| JP | 41-7786 | 4/1966 |
| JP | 41-7787 | 4/1966 |
| JP | 2001-302668 | 10/2001 |
| WO | WO 01/14382 | 3/2001 |
| WO | WO 01/74819 | 4/2001 |
| WO | 2004/022564 A2 | 3/2004 |
| WO | WO 2004/043964 | 5/2004 |
| WO | 2004/082620 A2 | 9/2004 |
| WO | WO 2004/085058 | 10/2004 |
| WO | WO 2005/0028483 | 3/2005 |
| WO | WO 2005/100361 | 10/2005 |
| WO | WO 2006/035195 | 4/2006 |
| WO | WO 2006/052710 | 5/2006 |
| WO | WO 2006/096626 | 9/2006 |
| WO | WO 2006/127899 | 11/2006 |
| WO | 2007/014137 A2 | 2/2007 |
| WO | WO 2009/012005 A1 | 1/2009 |
| WO | WO2010/144641 | 12/2010 |

OTHER PUBLICATIONS

Brine et al., "Formamidinesulfinic Acid Reduction of Dihydrocodeinone Derivatives", J. Org. Chem., vol. 43, No. 8, 1978, p. 1555-1557.
Burke et al., "Probes for narcotic Receptor Mediated Phenomena . . .", Heterocycles, vol. 23, No. 1, 1985, p. 99-110.
Butora et al., "Chemoenzymatic Synthesis of the Morphine Skeleton via Radical . . .", Tetrahedron Letters, vol. 37, No. 45, 1996, p. 8155-8158.
Campbell et al., "The Preparation of Unsymmetrical Secondary Aliphatic Amines", Jan. 1944, vol. 66, p. 82-84.
Chatterjie et al., "Reduction of 6-Ketones of the Morphine Series . . .", J. Org. Chem., vol. 41, No. 22, 1976, p. 3624-3625.
De Benneville et al., "The Behavior of aliphatic Aldehydes in the Leuckart-Wallach Reaction", J. Am. Chem. Soc., 1950, 72, pp. 3073-3075.
De Costa et al., "Probes for Narcotic Receptor Mediated Phenomena . . .", J. Med. Chem., 19972, 35, p. 2826-2835.
Farber et al., "A Synthesis of Armepavine and Related Bases. Resolution of (±)—Armepavine", Anales. Asoc. Quim. Argentina, 58, 1970, pp. 133-138.
Farber et al., "Resolution of (±)—armepavine", Chemistry and Industry, Jan. 13, 1968, pp. 57-58.
Fuiji et al., "The First Example of the Stereoselective Synthesis of . . .", Chem. Pharm. Bull., 52(6) , 2004, p. 747-750.
Fuiji et al., "Ruthenium(II)—Caatalyzed Asymmetric Transfer . . .", J. Am. Chem. Soc., 1996, 118, p. 2521-2522.
Gao et al., "Synthesis of 7-Arylmorphinans . . .", J. Med. Chem., 1998, 41, p. 3901-3098.
Gorlitzer et al., "Diepoxy-bis-(iminoethano)—dinaphth[2,1-b:1',2'-l]acridine [2, 3 +]", Arch. Pharm. (Weinheim) 325, 1992, p. 637-641.
Greene et al., "Protection for Phenols", Protective Groups in Organic Synthesis, 3rd, Ed., c1999, pp. 249-257and 266-269.
Gribble et al., "Reactions of Sodium Borohydride in Acidic Media . . .", Communications, Aug. 1987, p. 709-711.
Hashiguchi et al., "Asymmetric Transfer Hydrogenation of Aromatic ketones Catalyzed by chiral Ruthenium(II) Complexes", J. Am. Chem. Soc., vol. 177, No. 28, 1995, p. 7562-7563.
Huang et al., "Synthesis of (+−)—Glaucine and (+−)—Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Kalimin et al., "Palladium-Catalyzed 2-Phenylethenylation of Codeine . . .", Helevetica Chimca Acta, vol. 89, 2006, p. 861-869.
Kametani et al., "131. Coclaurine 7-Benzyloxy-1,2,3,4-tetrahydro-1-(p-hydroxyphenyl)-6- methoxy-2-methylisoquinoline 7-Benzyloxy-1,2,3,4-tetrahydro-1-(p-hydroxybenzyI)-6-methoxy-2-methylisoquinoline", Coclaurine, vol. 87, No. 7, 1967, pp. 757-760.
Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760, English Translation.
Kashdan et al., "Synthesis of 1,2,3,4-Tetrahydroisoquinolines", J. Org. Chem., 1982, 47, pp. 2638-2643.
Kirby et al,, "Synthesis of 14B-Mercaptocodeine Derivatives from N-t-Butoxycarbonyl-N-northebaine", Journal of chemical Research. Miniprint., 1984, pp. 2073-2086, XP9127313.
Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.
Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23; No. 44, pp. 4581-4584.
Koolpe et al., "Opioid Agonists and Antagonists. 6-Desoxy-6-substituted . . .", J. Med. Chem., 1985, 28(7), p. 949-957.
Lau et al., "Evolutiion of a Series of Non-Quinoline Leukotriene $D_4$ Receptor Antagonist . . ." , Bioorganic & Medicinal chemistry Letters, vol. 5, No. 15, 1995, p. 1615-1620.
Lazar et al., "A Selective Removal of Benzyl Protecting Groups in Arylphosphate Esters with Bromotrimethylsilane", Synthetic Communications, 22(6), 1992, p. 923-931.
Leland et al., "Analgesic narcotic antagonists. 5. 7,7-Dimethyldihydrocodeinones . . .", J. Med. Chem.., 1981, 24, p. 717-721.
Lespagnol et al., "Préparation d'amides de l'homovératrylamine et d'acids iodophénylacétiques substitués", Chim. Therap., 1965, p. 14-16.
Lespagnol at al., "Preparation of amides from the homoveratrylamine and iodephenylacetic substituted acids", Chim. Therap., 1965, pp. 14-16, English Translation by Fast-Trans.
Malspeis et al., "Metabolic Reduction of Naltrexone I. Synthesis, Separation . . .", Res. Commun. Chem. Pathol. Pharmacol, 2(43), 1975.
Mao et al., "A Chiral Rhodium Complex for Rapid Asymmetric Transfer . . .", Organic Letters, 1999, vol. 1, No. 6, p. 841-843.
Meuzelaar et al., "Chemistry of Opium Alkaloids, 45 Improvements in the Total Synthesis of Morphine", Eur. J. Org. Chem., 1999, pp. 2315-2321.
Mohamed of al., "Stereoselectivity of the Reduction of Naltrexone Oxime with Borane", Journal of Organic chemistry, 1986, 51(1), pp. 105-106.
Nagase et al., "The Facility of Formation of a $\Delta^6$ Bond in Dihydromorphinone and Related Opiates", J. Org. Chem., 1989, 54, p. 4120-4125.
Nagata et al., "Synthetic Studies on Isoquinoline Alkaloids. I. An Efficient Synthesis of 9,10—Substituted Protoberberine Alkaloids", Chem. Pharm. Bull., 194, 23(11), pp. 2867-2877.
Noyori et al., "Asymmetric Catalysts by Architechtural and Functional Molecular . . .", Agew. Chem. Int., Ed. 2001, 40, p. 40-73.
Noyori et al., "Asymmetric Transfer Hydrogenation Catalyzed by Chiral Ruthenium Complexes", Acc. Chem. Res., 1997, 30, p. 97-102.
Ohno at al., "Solid-Phase synthesis of 6-Sulfionylamino Morphinan Libraries", Synlett, 2002, No. 1, p. 93-96.
Olfoson et al., "A New Reagent for the Selective, High-Yield N-Dealkylation of Teritary Amines: Improved Syntheses of Naltrexone and Nalbuphine", J. Org. Chem.., 1984, 49, p. 2081-2082.
Olieman at al., "Conversion of (-)—dihydrocodeinone into . . .", Laboratory of Organic chemistry Technische Hogeschool Delft, Julianalaan 136, Delft, The Netherlands, Mar. 15, 1976.
Olsen at al., "Conjugate Addition Ligands of Opioid Antagonists . . .", J. Med. Chem., 1990, 33(2), p. 737-741.
Palmer et al., "Asymmetric transfer hydrogenation of C=O and C=N bonds", Tetrahedron: Asymmetry 10, 1999, p. 2045-2061, XP 004174087.

(56) References Cited

OTHER PUBLICATIONS

Puntener et al., "New Efficient Catalysts for enantioselective Transfer Hydrogenations", Tet. Lett., 1996, 37(45), pp. 8165-8168.
Sagara et al., "Specific Affinity Labeling of . . .", Bioorganic & Medicinal Chemistry Letters, vol. 5, No. 15, 1995, p. 1609-1614.
Saunders et al., "Assessment of relative nutritive value of proteins using streptoccus zymogenes", Chemistry and Industry, Jan. 13, 1968, pp. 56-58.
Sayre et al., "Stereospecific synthesis of the 6a- and 6b-Amino Derivatives of Naltrexone and Oxymorphone", J. Org. Chem., 1980, 45, pp. 3366-3368.
Schellenberg, "The Synthesis of Secondary and Tertiary Amines by Borohydride Reduction", Nov. 1963, p. 3259-3261.
Schmidhammer, "134. Synthesis and Biological ion of 14-Alkoxymorphinans Part $4^1$) Opioid Agonists and Partial Opioid Agonists in a Series of . . .", Helevitca Chimca Acta, vol. 72, 1989, p. 1233-1239.
Schütz et al., "Synthesis of 6-amino Acid Substituted Derivatives of the Highly Potent Analgesic 14-O-methyloxymorphone", Helvetica Chimica Acta, 2003, 86(6), pp. 2142-2148.
Seki, "Studies on the Morphine Alkaloids . . .", vol. 84, No. 7, p. 626-631.
Seki, "Studies on the Morphine Alkaloids . . .", vol. 84, No. 7, p. 626-631, English Translation.
Sheth et al., "Synthesis of N—(3',4'-Dimethoxy-5'-bromophenethyl)-2-(4-hydrioxyphenyl)—acetamide & Allied Products", Indian Journal of Chemistry, vol. 15B, Jul. 1977, pp. 595-598.
Simon et al., "Stereoselective Synthesis of β-naltrexol,β-naloxol, β-naloxamine, β-naltrexamine and Related Compounds by the Application of the Mitsunobu Reaction", Tetrahedron, 1994, 50(32), pp. 9757-9768.
Small et al., "The Addition of Organomagnesium Halides to Pseudocodeine Types. IV. Nuclear-Substituted Morphine Derivatives", Contribution from the Cobb Chemical Laboratory, University of Virginia, Received Jun. 6, 1938, pp. 204-232.
Spadoni et al., "2-[N-Acylamino($C_1$-$C_3$)alkyl]indoles as $MT_1$ . . .", J. Med. Chem., 1998, 41, p. 3624-3634.
Tolkachev et al., "Synthetic Investigation in [Kurarealkaloidov] Area XVI. Synthesis 1-(e'-Bromine . . .", Organicheskoi Khimii, 1966, 36(10), pp. 1767-1772.
Tolkachev et al., "Synthetic Investigation in [Kurarealkaloidov] Area XVI. Synthesis 1-(e'- Bromine . . .", Organicheskoi Khimii, 1966, 36(10), pp. 1767-1772, English Translation provided by Fast-Trans.
Uba et al., "Stereospecific Synthesis of Codeine . . .", Chem. Pharm. Bull., vol. 27, Issue 9, 1979, p. 2257-2258.
Uematsu et al., "Asymmetric Transfer Hydrogenation of Imines", J. Am. Chem. Soc., 1996, 118, p. 4916-4917.
Uwai et al., "Syntheses and receptor-binding studies of derivatives . . .", Bioorganic & Medicinal Chemistry, 12, 2004, p. 417-421, XP 002488979.
H.C. van der Plas et al., "On the reaction of 2-, 3- and 4-bromo(chloro)—1,8-naphthyridine with potassium amide in liquid ammonia", Laboratory of Organic Chemistry, Agricultural University, Wagenagen, The Netherlands, (Received Oct. 10, 1977).
Van Gurp et al., "Synthesis of 7,8-Didehydro-3,4-Dimethoxy . . .", Bull. Soc. Chim. Belg., vol. 96/n° Apr. 1987, p. 325-329.
Venkov et al., "Synthesis of isoquinolines from 2-phenylethylamines, amides, nitriles and carboxylic acids in polyphosphoric acid", Tetrahedron 19960909 GB, vol. 52, No. 37, Sep. 9, 1996, pp. 12299-12308, XP 002476120.
Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Watanabe et al., "Novel Synthesis of the Ortho Ester Derivative of 4,5-Epoxymorphinan", Organic Letters, vol. 8, No. 3, 2006, p. 523-526.
White et al., "Asymmetric Total Synthesis of (+)—Codeine via . . .", J. Org. Chem., 1999, 64, p. 7871-7884.
White et al., "Asymmetric Synthesis of (+)—Morphine . . .", J. Org. Chem., 1997, 62, p. 5250-5251.
Wu et al., "Asymmetric transfer hydrogenation of imines and iminiums . . .", Chem. Commun., 2006, p. 1766-1768.
Yamakawa et al., "The Methal-Ligand Bifunctional Catalysis: A Theoretical Study on . . .", J. Am. Chem. Soc., 2000, 122, p. 1466-1478.
Takemori et al. "Stereochemical Studies on Medicinal Agents . . .," Journal of Medicinal Chemistry, 1977, 20(8), pp. 1100-1102.
Reddy et al., "A convenient method for the N-formylation of secondary amines . . .", JTetrahedron Letters, 41, 2000, pp. 9149-9151.
Kelentey et al., "Preparation and pharmacological properties of n-oxides of opium alkaloids", Kiserletes orvostudomany, 1958, 10(1), pp. 70-77.
Kelentey et al., "Preparation and pharmacological studies of n-oxides of opium alkaloids", Arzneimittel-Forschung, 1957, 7, pp. 594-597.
Takagi et al., "Antitussive Activity of the N-Oxides of Opium Alkaloids", Journal of the Pharmaceutical Society of Japan, 77(11), 1957 p. 1358.
Takagi et al., "Studies on Antitussives. II. Opium Alkaloids and their N-Oxides", Journal of the Pharmaceutical Society of Japan, 80(10), 1960, pp. 1501-1506.
Heumans et al., "Some aspects of the metabolism of morphine-N-oxide", J. Pharm. Pharmac., 1971, 23, pp. 831-836.
Bao et al., "Morphinane Alkaloids with Cell Protective Effects from *Sinomenium acetum*", J. Nat. Prod., 2005, 68, pp. 1128-1130.
Makareviche et al., "Quaternary Salts of Alkaloids", Chemistry of Natural Compounds, 2006, 42(4), pp. 473-476.
Dolle, et al. (Document No. 144:397383, CAPLUS) 2006.
Tanabe (Document No. 144:445378, CAPLUS) 2006.
Schoenecker et al.; J. Med. Chem.; "Irreversible Blockage of Opioid Receptor Types by Ester Homologues of beta-Funaltrexamine"; 1986, 29, 1868-1871.
Schoenecker et al.; J. Med. Chem.; "Opioid Agonist and Antagonist Activities of Monofunctional Nitrogen Mustard Analogues of beta-chlornaltrexamine"; 1987, 30, 933-935.
Portoghese et al.; J. Med. Chem. ; "Synthesis and Biological Activity of Analogues of beta-chlornaltrexamine and beta-funaltrexamine at opioid receptors", 1986, 29, 1861-1864.
Portoghese et al.; J. Med. Chem.; "Synthesis and Opioid Antagonist Potencies of Naltrexone Bivalent ligands with conformationally restriced spacers"; 1986, 29, 1650-1653.
Mohamed et al.; J. Med. Chem.; "Activity of N-Methyl-alpha- and beta-funaltrexamine at opioid receptors", 1986, 29, 1551-1553.
Mohamed et al.; J. Org. Chem.; "Stereoselectivity of the reduction of naltrexone oxime with borane", 1986, 51, 105-106.
Jiang et al.,; Journal of Medicinal Chemistry; "Stereochemical studies on medicinal agents. 23. Synthesis and biological evaluation of 6-amino derivatives of naloxone and naltrexone", 1977, vol. 20, No. 8.
Sayre et al. ; J. Org. Chem.; "Stereospecific Synthesis of the 6 alpha- and 6 beta-amino derivatives on naltrexone and oxymorphone"; 1980, 45, 3366-3368.
Aceto et al., "Stereoselective μ- and 6-opioid receptor-related antinociception and binding with (+)-thebaine", European Journal of Pharmacology, 1999, pp. 143-147, vol. 365.
Office Action from related European Patent Application No. 10704729.2, dated Feb. 28, 2014, 5 pgs.
Office Action from related Japanese Patent Application No. 2011-551283, dated May 2, 2014, 5 pgs.
First Office Action from related Chinese Patent Application No. 201080008777.2, dated May 20, 2013, 5 pgs.
Second Office Action from related Chinese Patent Application No. 201080008777.2, dated Dec. 23, 2013, 6 pgs.
Third Office Action from related Chinese Patent Application No. 201080008777.2, dated Jul. 03, 2014, 6 pgs.

(+)-6-HYDROXY-MORPHINAN OR (+)-6-AMINO-MORPHINAN DERIVATIVES

CROSS REFERENCE TO RELATED APPLICATIONS

This application is a continuation-in-part of U.S. patent application Ser. No. 12/710,390, filed Feb. 23, 2010, now U.S. Pat. No. 8,563,724, which claims the benefit of U.S. Provisional Application No. 61/154,449, filed Feb. 23, 2009, each of which is hereby incorporated by reference in its entirety.

FIELD OF THE INVENTION

The present invention generally relates to substituted (+)-6-hydroxy-morphinans or substituted (+)-6-amine-morphinans and methods of using substituted (+)-6-hydroxy-morphinans or substituted (+)-6-amine-morphinans to inhibit microglial activation in the central nervous system.

BACKGROUND OF THE INVENTION

Microglia serve as the first and main form of active immune defense in the central nervous system. These cells are believed to be functionally equivalent to monocytes or tissue macrophages of the somatic immune system. It has long been recognized that microglia migrate to, differentiate and proliferate at sites of brain injury and inflammation. Thus, activation of microglia appears to play a major role in numerous neuroinflammatory diseases or disorders. Furthermore, microglial activation is modulated by opiates and has been implicated in opiate dependence and the development of tolerance. The mu opiate receptor antagonists, (−)-naloxone and (−)-naltrexone, have been shown to inhibit the proinflammatory pathway involved in microglial activation. Inhibition of microglial activation is non-stereoselective, however, in that the (+) mirror enantiomers of naloxone and naltrexone have been shown to retain microglial inhibitory activity. Thus, (+)-morphinan compounds may be useful for treating inflammatory diseases, as antitussive agents, or for reducing the potential of opiate abuse and dependence. Substitution at position 6 of the morphinan ring may provide compounds that function as prodrugs with increased activity relative to the unfunctionalized precursors. There is a need, therefore, for mirror image enantiomorph (+)-morphinan compounds with substituted hydroxy or amino groups at position 6.

SUMMARY OF THE INVENTION

The present invention provides processes for preparing substituted (+)-6-beta morphinans. In general, the process disclosed herein comprises condensing a 6-keto morphinan with a secondary amine to form an enamine intermediate, which is then reduced to form a substituted 6-beta-amino morphinan.

Accordingly, one aspect of the present invention encompasses a process for preparing a (+)-morphinan compound of Formula (IV). The process comprises (a) contacting a compound of Formula (III) with a secondary amine comprising $NHR^8R^9$ and an acid catalyst to form an intermediate enamine compound; and (b) or contacting the intermediate enamine compound with sodium cyanoborohydride to form the compound of Formula (IV) according to the following reaction scheme:

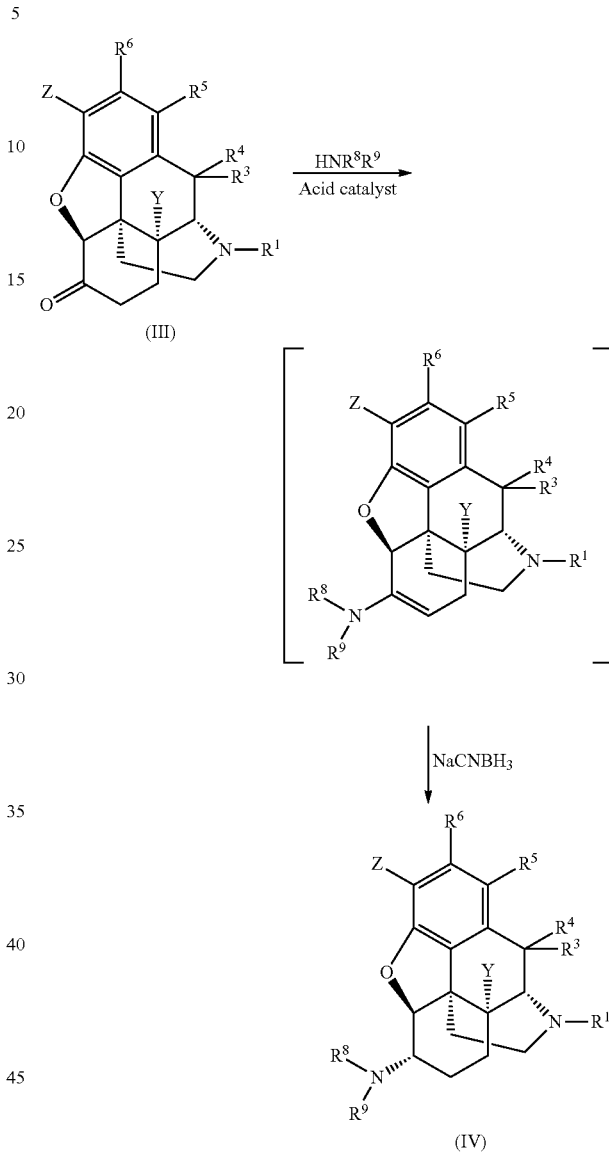

wherein:

$R^1$ is chosen from hydrocarbyl and substituted hydrocarbyl;

$R^3$ and $R^4$ are independently chosen from hydrogen, hydrocarbyl, and substituted hydrocarbyl;

$R^5$ and $R^6$ are independently chosen from hydrogen, hydrocarbyl, substituted hydrocarbyl, halogen, {—}OH, {—}NH$_2$, and {—}OR$^7$;

$R^7$ is chosen from hydrocarbyl and substituted hydrocarbyl;

$R^8$ and $R^9$ are independently chosen from acyl, acyloxy, alkyl, cycloalkyl, alkoxy, hydroxy alkyl, alkenyl, aryl, aryloxy, substituted alkyl, substituted cycloalkyl, substituted alkenyl, substituted aryl, and together $R^8$ and $R^9$ form a ring or ring system chosen from carbocyclic, substituted carbocyclic, heterocyclic, substituted heterocyclic, and a combination thereof; provided that when one of $R^8$ or $R^9$ is benzyl, then the other of $R^8$ or $R^9$ is other than $C_1$-$C_5$ alkyl or $C_6$-$C_{12}$ aryl;

Y is chosen from hydrogen, hydroxy, protected hydroxy, alkoxy, and acyloxy; and

Z is chosen from hydroxy, protected hydroxy, alkoxy, and acyloxy.

Other aspects and iterations of the invention are described in more detail below.

DETAILED DESCRIPTION OF THE INVENTION

The present invention provides substituted (+)-6-hydroxy-morphinans or substituted (+)-6-amino-morphinans. The compounds of the present invention are mirror image enantiomers of naturally occurring opiate alkaloids. The substituted (+)-6-hydroxy- or (+)-6-amino-morphinans preferentially bind to glia (i.e., microglia and astrocytes) of the central nervous system and inhibit their activation.

(I) Substituted (+)-6-Hydroxy- or 6-Amino-Morphinan Compounds (a) Compounds Comprising Formula (II)

One aspect of the present invention encompasses a compound comprising Formula (II) or a pharmaceutically acceptable salt thereof:

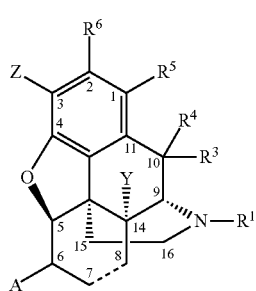
(II)

wherein:

A is selected from the group consisting of {—}$OR^8$ and {—}$NR^8R^9$;

$R^1$ is selected from the group consisting of hydrocarbyl and substituted hydrocarbyl;

$R^3$, $R^4$, $R^8$, and $R^9$ are independently selected from the group consisting of hydrogen, hydrocarbyl, and substituted hydrocarbyl;

$R^5$ and $R^6$ are independently selected from the group consisting of hydrogen, hydrocarbyl, substituted hydrocarbyl, halogen, {—}OH, {—}$NH_2$, and {—}$OR^7$;

$R^7$ is selected from the group consisting of hydrocarbyl and substituted hydrocarbyl;

Y is selected from the group consisting of hydrogen, hydroxy, protected hydroxy, alkoxy, and acyloxy;

Z is selected from the group consisting of hydroxy, protected hydroxy, alkoxy, and acyloxy; and the dashed line between the carbon atoms at positions 7 and 8 represents a single bond or a double bond.

In preferred iterations, $R^3$, $R^4$, $R^5$, and $R^6$ are each hydrogen.

In one embodiment of this aspect of the invention, the compound comprises Formula (IIa) or a pharmaceutically acceptable salt thereof:

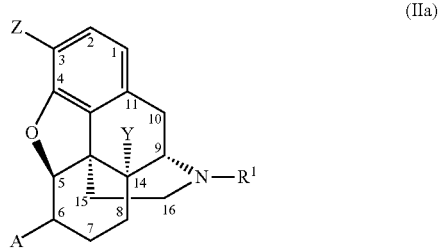
(IIa)

wherein:

A, $R^1$, $R^8$, and $R^9$, Y and Z are as defined above for compounds comprising Formula (II).

Representative compounds comprising Formula (IIa) or pharmaceutically acceptable salts thereof include (+)-nalbuphine and (+)-nalfurafine.

In another embodiment of this aspect of the invention, the compound comprises Formula (IIb) or a pharmaceutically acceptable salt thereof:

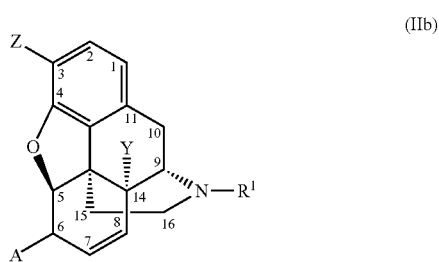
(IIb)

wherein:

A, $R^1$, $R^8$, and $R^9$, Y and Z are as defined above for compounds comprising Formula (II).

In each of the embodiments for compounds comprising Formula (II), (IIa) or (IIb), provided, however, that when A is {—}OH, {—}O(CO)$CH_3$, {—}NH(CH$_2$)$_2$OH, {—}NH(CO)$CH_3$, or {—}$NH_2$, then $R^1$ is other than methyl.

In each of the for compounds comprising Formula (II), (IIa) or (IIb), provided, however, that when A is {—}OH, {—}NH(CH$_2$)$_2$OH, or {—}NH(CO)$CH_3$, then $R^1$ is other than {—}CH$_2$(CH)CH$_2$.

In each of the embodiments for compounds comprising Formula (II), (IIa) or (IIb), provided, however, that when A is {—}OH, {—}NCH$_3$(CO)CH(CH)(CH)$_4$O, {—}NH(CH$_2$)$_2$OH, {—}NH(CO)$CH_3$, {—}$NH_2$, or {—}NHCH$_3$ then $R^1$ is other than {—}CH$_2$(cyclopropane).

In each of the embodiments for compounds comprising Formula (II), (IIa) or (IIb), provided, however, that when A is {—}OH, then $R^1$ is other than {—}CH$_2$(cyclobutane).

(b) Compounds Comprising Formula (I)

Another aspect of the present invention encompasses a compound comprising Formula (II) or a pharmaceutically acceptable salt thereof:

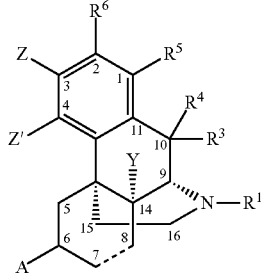

(I)

wherein:

A is selected from the group consisting of {—}OR$^8$ and {—}NR$^8$R$^9$;

R$^1$ is selected from the group consisting of hydrocarbyl and substituted hydrocarbyl;

R$^3$, R$^4$, R$^8$, and R$^9$ are independently selected from the group consisting of hydrogen, hydrocarbyl, and substituted hydrocarbyl;

R$^5$ and R$^6$ are independently selected from the group consisting of hydrogen, hydrocarbyl, substituted hydrocarbyl, halogen, {—}OH, {—}NH$_2$, and {—}OR$^7$;

R$^7$ is selected from the group consisting of hydrocarbyl and substituted hydrocarbyl;

Y is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed line between the carbon atoms at positions 7 and 8 represents a single bond or a double bond.

In preferred iterations, R$^3$, R$^4$, R$^5$, and R$^6$ are hydrogen.

In one embodiment of this aspect of the invention, the compound comprises Formula (Ia) or a pharmaceutically acceptable salt thereof:

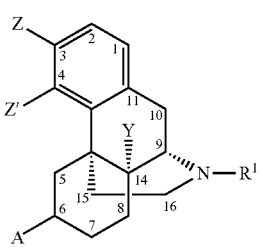

(Ia)

wherein:

A, R$^1$, R$^8$, and R$^9$, Y, Z and Z' are as defined above for compounds comprising Formula (I).

In a further embodiment of this aspect of the invention, the compound comprises Formula (Ib) or a pharmaceutically acceptable salt thereof:

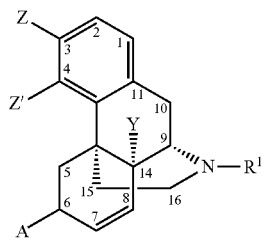

(Ib)

wherein:

A, R$^1$, R$^8$, and R$^9$, Y, Z and Z' are as defined above for compounds comprising Formula (I).

In preferred iterations of the afore-mentioned embodiments, R$^1$ is alkyl, cycloalkyl, cycloalkylmethyl, alkenyl, alkynyl, or aryl. In more preferred iterations, R$^1$ is cyclopropylmethyl, cyclobutylmethyl, allyl, propargyl, or benzyl. Preferably, A is hydroxy, alkoxy, acyloxy, amine, alkyl substituted amine, amido, carbamyl (i.e., {—}OCNH$_2$), carbonate, or urea. In iterations wherein A is alkoxy, the alkyl substituent is preferably lower alkyl. In iterations wherein A is acyloxy (i.e., {—}OC(═O)R), the R substituent is hydrogen, hydrocarbyl, substituted hydrocarbyl, or hetercyclo. In iterations wherein A is an amine (i.e., {—}NR'R"), R' is hydrogen, hydrocarbyl, or substituted hydrocarbyl, and R" is hydrocarbyl, or substituted hydrocarbyl. In iterations wherein A is an alkyl substituted amine, the alkyl is preferably lower alkyl. In iterations wherein A is amido (i.e., {—}N'R'(═O)R"), the R substituents generally are independently hydrogen, lower alkyl, substituted lower alkyl, lower alkenyl, or substituted lower alkenyl. In iterations wherein A is carbonate (i.e., {—}OC(═O)R or {—}NR'C(═O)R"), the R groups are independently hydrogen, hydrocarbyl, or substituted hydrocarbyl. In iterations in which A is urea (i.e., {—}NR'C(═O)NHR"), the R groups are independently hydrogen, hydrocarbyl, or substituted hydrocarbyl.

Each of the compounds comprising Formulas (II), (IIa), (IIb), (I), (Ia), (Ib), or a pharmaceutically acceptable salt thereof has a (+) orientation with respect to the rotation of polarized light. More specifically, each chiral center has an R or an S configuration. In particular, the carbon at position 5, if chiral, has an S configuration, the carbon at position 13 has an R configuration, the carbon at position 14 has an R configuration, and the carbon at position 9 has an S configuration. Furthermore, the carbon at position 6 may comprise an S or an R configuration. Stated another way, the substituted ring at position 5, if present, is in the beta position, and the Y group at position 14 is in the alpha position.

Pharmaceutically acceptable salts of compounds comprising Formulas (II), (IIa), (IIb), (I), (Ia), or (Ib) include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like.

(II) Methods for Inhibiting Activation of Microglia

Another aspect of the invention provides methods for inhibiting activation of microglia in a subject. The methods of the invention comprise administering to the subject a compound comprising Formulas (II), (IIa), (IIb), (I), (Ia), (Ib), or a pharmaceutically acceptable salt thereof. The compounds comprising Formulas (II), (IIa), (IIb), (I), (Ia), and (Ib) are detailed above in section (I).

The compound may be administered to the subject in accord with known methods. Typically, the compound will be administered orally, but other routes of administration such as parenteral or topical may also be used. The amount of compound that is administered to the subject can and will vary depending upon the type of compound, the condition being treated, the subject, and the particular mode of administration. Those skilled in the art will appreciate that dosages may be determined with guidance from Goodman & Goldman's The Pharmacological Basis of Therapeutics, Tenth Edition (2001), Appendix II, pp. 475-493, and the Physicians' Desk Reference.

(III) Process for Preparing Substituted (+)-6-Beta-Amino Morphinans

A further additional aspect of the present disclosure encompasses processes for preparing substituted (+)-6-beta-amino morphinans. In particular, the process comprises (a) forming a compound of Formula (IV) by contacting a compound of Formula (III) with a secondary amine comprising $NHR^8R^9$ and an acid catalyst to form an intermediate enamine compound, and (b) contacting the intermediate enamine compound with sodium cyanoborohydride to form the compound of Formula (IV) according to the following reaction scheme:

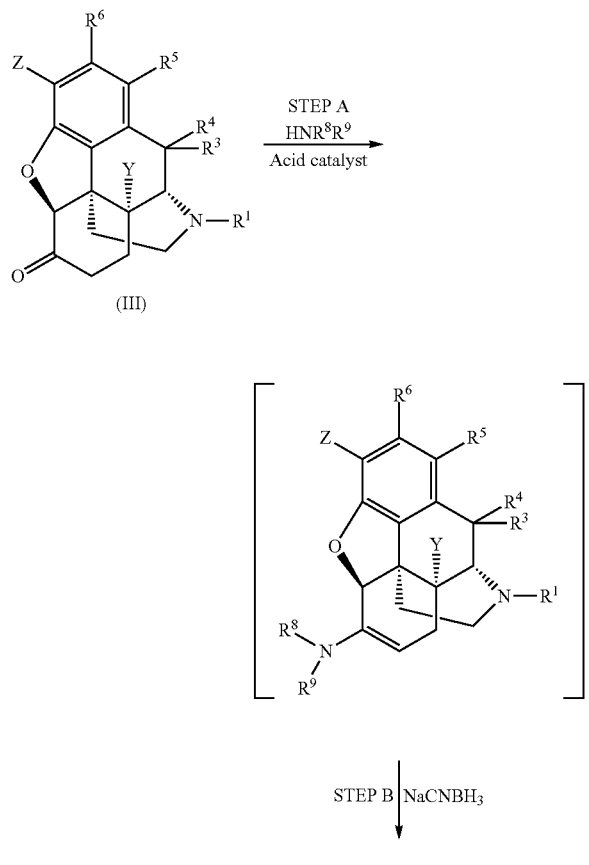

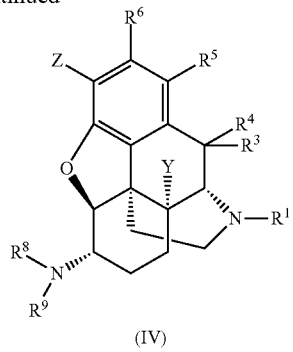

wherein:

$R^1$ is chosen from hydrocarbyl and substituted hydrocarbyl;

$R^3$ and $R^4$ are independently chosen from hydrogen, hydrocarbyl, and substituted hydrocarbyl;

$R^5$ and $R^6$ are independently chosen from hydrogen, hydrocarbyl, substituted hydrocarbyl, halogen, {—}OH, {—}$NH_2$, and {—}$OR^7$;

$R^7$ is chosen from hydrocarbyl and substituted hydrocarbyl;

$R^8$ and $R^9$ are independently chosen from acyl, acyloxy, alkyl, cycloalkyl, alkoxy, hydroxy alkyl, alkenyl, aryl, aryloxy, substituted alkyl, substituted cycloalkyl, substituted alkenyl, substituted aryl, and together $R^8$ and $R^9$ form a ring or ring system chosen from carbocyclic, substituted carbocyclic, heterocyclic, substituted heterocyclic, and a combination thereof; provided that when one of $R^8$ or $R^9$ is benzyl, then the other of $R^8$ or $R^9$ is other than $C_1$-$C_5$ alkyl or $C_6$-$C_{12}$ aryl;

Y is chosen from hydrogen, hydroxy, protected hydroxy, alkoxy, and acyloxy; and

Z is chosen from hydroxy, protected hydroxy, alkoxy, and acyloxy.

In some embodiments, $R^1$ may be alkyl, cycloalkyl, alkenyl, alkynyl, aryl, substituted alkyl, substituted cycloalkyl, substituted alkenyl, substituted alkynyl, or substituted aryl. In specific embodiments, $R^1$ may be methyl, ethyl, cyclopropylmethyl, cyclobutylmethyl, allyl, propargyl, or benzyl.

In exemplary embodiments, $R^1$ may be methyl, cyclopropylmethyl, cyclobutylmethyl, or allyl; $R^3$, $R^4$, $R^6$, and $R^6$ may be hydrogen; Y may be hydrogen, hydroxyl, or protected hydroxyl, and Z may be hydroxy, protected hydroxy or methoxy.

Each of the compounds of Formulas (III), (IV), and the intermediates described below has a (+) orientation with respect to the rotation of polarized light. More specifically, each chiral center has an R or an S configuration. Carbons are positions 5, 13, 14, and 9 are chiral. In particular, the carbon at position 5 has an S configuration, the carbon at position 13 has an R configuration, the carbon at position 14 has an R configuration, and the carbon at position 9 has an S configuration. Additionally, the carbon at position 6 of the compound of Formula (IV) has a beta configuration.

(a) Step A—Reaction Mixture

The first step of the process comprises condensing the 6-keto morphinan compound of Formula (III) with a secondary amine to form the enamine morphinan intermediate. The process commences with formation of a reaction mixture comprising the compound of Formula (III), the secondary amine comprising $NR^8R^9$, and the acid catalyst. In some embodiments, the reaction mixture further comprises a solvent or solvent system.

Compound of Formula (III) are detailed above.

(i) Secondary Amine Comprising NR$^8$R$^9$

As detailed above, R$^8$ and R$^9$ are independently chosen from acyl, acyloxy, alkyl, cycloalkyl, alkoxy, hydroxy alkyl, alkenyl, aryl, aryloxy, substituted alkyl, substituted cycloalkyl, substituted alkenyl, substituted aryl, and together R$^8$ and R$^9$ form a ring or ring system chosen from carbocyclic, substituted carbocylic, heterocyclic, substituted heterocyclic, and a combination thereof; provided that when one of R$^8$ or R$^9$ is benzyl, then the other of R$^8$ or R$^9$ is other than C$_1$-C$_5$ alkyl or C$_6$-C$_{12}$ aryl.

In various embodiments, R$^8$ and/or R$^9$ may be, without limit, formyl, acetyl, propionyl, butanoyl, benzoyl, acrylyl, acetoxy, benzoyloxy, methyl, ethyl, propyl, isopropyl, butyl, hexyl, heptyl, cyclopropyl, cyclobuty, cyclohexyl, cycloheptyl, methoxy, ethoxy, propoxy, butoxy, phenoxy, nriethylphenyloxy, hydroxymethyl, hydroxyethyl, hydroxypropyl, hydroxybutyl, hydroxyacetyl, hydroxyphenyl, hydroxymethylphenyl, ethenyl, propenyl, isopropenyl, butenyl, isobutenyl, hexenyl, ethynyl, propynyl, butynyl, isobutynyl, hexynyl, phenyl, methylphenyl, dimethylphenyl, benzyl, toluyl, indenyl, furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, or combinations thereof.

In other embodiments, R$^8$ and R$^9$ together may form a ring or ring system including, but not limited to, piperidine, morpholine, pyridine, piperazine, pyrimidine, pyridazine, pyrazine, purine, triazine, oxazine, oxathiazine, isoxazine, azepine, diazepine, indole, isoindole, cyclopentapyridine, indazole, indoxazine, benzoxazole, anthranil, quinolone, isoquinoline, cinnoline, quinazoline, naphthyridine, pyridopyridine, benzoxazine, carbazole, acridine, pyrrole, pyrazole, imidazole, triazole, thiazole, isothiazole, oxadiazole, dioxazole, or methyl, ethyl, acetyl, hydroxy, methoxy, or phenyl derivatives of any of the foregoing.

The amount of secondary amine comprising NHR$^8$R$^9$ that is added to the reaction mixture can and will vary. In general, the mole to mole ratio of the compound of Formula (III) to the secondary amine may range from about 1:0.5 to about 1:4. In various embodiments, the mole to mole ratio of the compound of Formula (III) to the secondary amine may range from about 1:0.5 to about 1:1.0, from about 1:1.0 to about 1:1.5, from about 1:1.5 to about 1:2.0, from about 1:2.0 to about 1:2.5, from about 1:2.5 to about 1:3.0, from about 1:3.0 to about 1:3.5, or from about 1:3.5 to about 1:4.0. In specific embodiments, the mole to mole ratio of the compound of Formula (III) to the secondary amine may range from about 1:1 to about 1:3. In exemplary embodiments, the mole to mole ratio of the compound of Formula (III) to the secondary amine may range from about 1:1.5 to about 1:2.

(ii) Acid Catalyst

A variety of acid catalysts are suitable for use in the process disclosed herein. In some embodiments, the acid catalyst may be a mineral acid. Suitable mineral acids include, without limit, hydrochloric acid, hydrobromic acid, hydroiodic acid, hypochloric acid, chloric acid, perchloric acid, periodic acid, sulfuric acid, fluorosulfuric acid, nitric acid, phosphoric acid, hexafluorophosphoric acid, chromic acid, boric acid, fluoroboric acid, or combinations thereof. In other embodiments, the acid catalyst may be a sulfonic acid. Non-limiting examples of suitable sulfonic acids include p-toluenesulfonic acid, methanesulfonic acid, ethanedisulfonic acid, benzenesulfonic acid, trifluromethanesulfonic acid, isopropylbenzenesulfonic acid, or combinations thereof. In exemplary embodiments, the acid catalyst may be p-toluenesulfonic acid.

The amount of acid catalyst added to the reaction mixture may vary. In general, the mole to mole ratio of the compound of Formula (III) to the acid catalyst may range from about 1:0.002 to about 1:0.5. In certain embodiments, the mole to mole ratio of the compound of Formula (III) to the acid catalyst may range from about 1:0.002 to about 1:0.01, from about 1:0.01 to about 1:0.05, from about 1:0.05 to about 1:0.2, or from about 1:0.2 to about 1:0.5. In specific embodiments, the mole to mole ratio of the compound of Formula (III) to the acid catalyst may range from about 1:0.005 to about 1:0.2. In exemplary embodiments, the mole to mole ratio of the compound of Formula (III) to the acid catalyst may range from about 1:0.01 to about 1:0.15.

(iii) Solvent or Solvent System

In some embodiments, the reaction mixture further comprises a solvent or solvent system. In general, the solvent or solvent system is immiscible with water. As used herein, "immiscible" means that in some proportion two phases are present. Non-limiting examples of solvents that are immiscible with water include benzene, n-butanol, butyl acetate, carbon tetrachloride, chloroform cyclohexane, 1,2-dichloroethane, dichloromethane, ethyl acetate, di-ethyl ether, heptane, hexane, methyl-1-butyl ether, methyl ethyl ketone, pentane, di-isopropyl ether, toluene, trichloromethane, xylene, and combinations thereof. The solvent system may comprise at least one solvent that is immiscible with water as well as a solvent(s) that is miscible in water. Examples of solvents miscible with water include, without limit, acetic acid, acetone, acetonitrile, dimethylformamide, dimethyl sulfoxide, dioxane, ethanol, methanol, n-propanol, isopropanol, and tetrahydrofuran. In exemplary embodiments, the solvent may comprise toluene.

In general, the volume to mass ratio of the solvent to the compound of Formula (III) may range from about 5:1 to about 200:1. In various embodiments, the volume to mass ratio of the solvent to the compound of Formula (III) may range from 5:1 to about 20:1, from about 20:1 to about 50:1, from about 50:1 to about 100:1, or from about 100:1 to about 200:1. In specific embodiments, the volume to mass ratio of the solvent to the compound of Formula (III) may range from about 15:1 to about 115:1. In exemplary embodiments, the volume to mass ratio of the solvent to the compound of Formula (III) may range from about 40:1 to about 80:1.

(b) Step A—Reaction Conditions

In general, the reaction may be conducted at a temperature that ranges from about 0° C. to about 150° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., from about 100° C. to about 120° C., or from about 100° C. to about 120° C. In other embodiments, the reaction may be conducted at reflux. For example, the temperature of the reaction may range from about 30° C. to about 130° C. In exemplary embodiments, the temperature of the reaction may range from about 100° C. to about 115° C.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of the starting keto compound and a significantly increased amount of the intermediate enamine compound compared to the amounts of each present at the beginning of the reaction.

Typically, the amount of the keto compound, i.e., the compound of Formula (III), remaining in the reaction mixture after the reaction is complete may be less than about 3%, or less than about 1%. In general, the reaction may proceed for at least about 10 hours. In some embodiments, the reaction may proceed for at least about 16 hours, at least about 20 hours, at least about 24 hours, at least about 36 hours, or at least about 48 hours.

Initially, condensation between the compound of Formula (III) and the secondary amine forms a hemiaminal intermediate, as shown below:

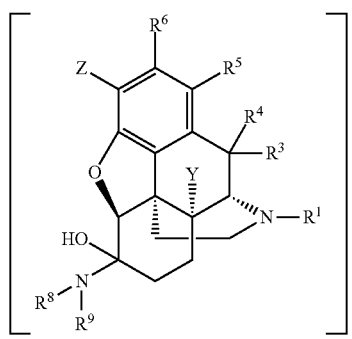

Dehydration of the hemiaminal intermediate forms the enamine intermediate. Typically the reaction is conducted in a Dean Stark trap, which facilitates removal of water. Alternatively, the reaction may be conducted under dehydrating conditions, which are well known in the art.

Upon completion of the reaction, the solvent may be removed from the reaction mixture comprising the enamine intermediate. The solvent may be removed by distillation, evaporation, decantation, or any suitable means.

(c) Step B—Reaction Mixture

The process further comprises reducing the enamine morphinan intermediate by contact with a reducing agent, such as sodium cyanoborohydride, to form the substituted 6-beta-amino morphinan of Formula (IV).

(i) Reducing Agent

A variety of reducing agents may be used in this step of the process. In some embodiments, the reducing agent may be sodium borohydride, potassium borohydride, lithium borohydride, lithium triethylborohydride, zinc borohydride, aluminum borohydride, calcium borohydride, magnesium borohydride, sodium triacetoxyborohydride, tetramethylammonium triacetoxyborohydride, boranepyridine, 2-picoline borane, 9-borabicyclo(3.3.1)nonane, sodium or potassium triethylborohyride, sodium or potassium triphenylborohydride, lithium bis(triphenylphosphine)copper borohydride, lithium morphilinoborohydride, or lithium pyrrolidinoborohydride. In general, reduction with one of the above listed reducing agents forms both the 6-alpha and 6-beta isomers of the substituted 6-amino compound. The 6-beta epimer may be separated from the 6-alpha epimer using standard separation techniques.

In exemplary embodiments, the reducing agent may be an alkali metal sodium cyanoborohydride. Reduction of the enamine intermediate with an alkali metal cyanoborohydride forms the 6-beta isomer and an unstable cyano compound, which is diagrammed below.

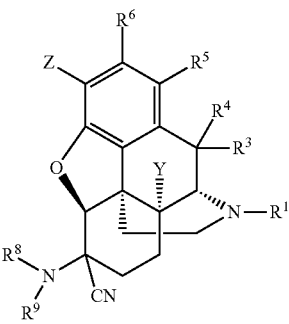

Essentially no 6-alpha isomer is formed when the enamine intermediate is contacted with an alkali metal cyanoborohydride. In general, the ratio of the 6-beta isomer to the cyano compound is greater than about 80:20. In some embodiments, the ratio of the 6-beta isomer to the cyano compound may be greater than about 90:10, greater than about 95:5, greater than about 99:1, greater than about 99.5:0.5, or greater than about 99.9:0.1. The 6-beta isomer may be isolated from the unstable cyano compound using standard techniques. For example, the 6-beta isomer may be isolated by column chromatography.

The alkali metal cyanoborohydride may be sodium cyanoborohydride, potassium cyanoborohydride, or lithium cyanoborohydride. In exemplary embodiments, the metal cyanoborohydride is sodium cyanoborohydride.

The amount of reducing agent used in the process can and will vary. In general, the mole to mole ratio of the compound of Formula (III) to the reducing agent ranges from about 1:0.2 to about 1:4. In certain embodiments, the mole to mole ratio of the compound of Formula (III) to the reducing agent may range from about 1:0.2 to about 1:1, from about 1:1 to about 1:1.5, from about 1:1.5 to about 1:2, or from about 1:2 to about 1:4. In embodiments in which the reducing agent is sodium cyanoborohydride, the mole to mole ratio of the compound of Formula (III) to sodium cyanoborohydride may range from about 1:0.5 to about 1:3. In specific embodiments in which the reducing agent is sodium cyanoborohydride, the mole to mole ratio of the compound of Formula (III) to sodium cyanoborohydride may range from about 1:1 to about 1:2.

(ii) Solvent or Solvent System

In some embodiments, the solvent or solvent system used during step A of the process also may be used in step B of the process. In other embodiments, the solvent or solvent system used during step A of the process may be removed and a different solvent or solvent system may be used in step B of the process. For example, the solvent or solvent system used during step B may be an alcohol such as, for example, methanol, ethanol, propanol, or isopropanol. In exemplary embodiments, step B of the process may be conducted in the presence of ethanol.

The amount of solvent present during step B of the process may vary. In general, the volume to mass ratio of the solvent to the compound of Formula (III) ranges from about 1:1 to about 100:1. In some embodiments, the volume to mass ratio of the solvent to the compound of Formula (III) may range from 1:1 to about 5:1, from about 5:1 to about 15:1, from about 15:1 to about 40:1, or from about 40:1 to about 100:1. In specific embodiments, the volume to mass ratio of the solvent to the compound of Formula (III) may range from about 2:1 to about 50:1.

(d) Step B—Reaction Conditions

In general, the reaction may be conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. In certain embodiments, the temperature of the reaction may range from about 20° C. to about 80° C. In specific embodiments, the reduction reaction of step B may be conducted at room temperature.

Typically, the reaction is allowed to proceed for a sufficient period of time until the reaction is complete, as detailed above. Typically, the amount of the enamine intermediate remaining in the reaction mixture after the reaction is complete may be less than about 3%, or less than about 1%. In general, the duration of the reaction may range from about several hours to several days. In some embodiments, the duration of the reaction may range from about 3 hours to about 12 hours, from about 12 hours to about 24 hours, from about 24 hours to about 48 hours, from about 48 hours to about 72 hours, or from about 72 hours to about 96 hours.

In some embodiments, the compound of Formula (IV) may be isolated from the reaction mixture using techniques known to those of skill in the art. Non-limiting examples of suitable techniques include precipitation, extraction, evaporation, distillation, chromatography, and crystallization. In certain embodiments, the compound of Formula (IV) may be separated from the cyano compound as detailed above.

The yield of the compound of Formula (IV) can and will vary. Typically, the yield of the compound of Formula (IV) may be at least about 40%. In one embodiment, the yield of the compound of Formula (IV) may range from about 40% to about 60%. In another embodiment, the yield of the compound of Formula (IV) may range from about 60% to about 80%. In a further embodiment, the yield of the compound of Formula (IV) may range from about 80% to about 90%. In still another embodiment, the yield of the compound of Formula (IV) may be greater than about 90%, or greater than about 95%.

In some embodiments, the compound of Formula (IV) may be further reacted with suitable reagents to dealkylate the amine group, thereby converting the tertiary amine into a primary amine. For example, benzyl groups can be removed by contact with hydrogen gas (~40 psi) and a transition metal catalyst (i.e., 10% Pd/C). Persons skilled in the art are familiar with other means for removing hydrocarbyl or substituted hydrocarbyl groups from tertiary amines (e.g., via contact with acid halides). The compound comprising a 6-beta-amino group may be functionalized by contact with electrophiles, such as alkyl halides, or contact with aldehydes or aldehyde dimers to form tertiary amines at the 6-beta position.

The compound of Formula (IV) or its derivatives may be converted into pharmaceutically acceptable salts using standard procedures. The term "pharmaceutically acceptable salts" are salts commonly used to form alkali metal salts or addition salts of free acids or free bases. The nature of the salt may vary, provided that it is pharmaceutically acceptable. Suitable pharmaceutically acceptable acid addition salts of compounds of Formula (IV) or derivatives thereof may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts of compounds of Formula (IV) or derivatives thereof include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with the any of the compounds of the invention.

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses "aryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl is the preferred aryl.

The terms "halogen" or "halo" as used herein alone or as part of another group refer to chlorine, bromine, fluorine, and iodine.

The term "heteroatom" refers to atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkynoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom, wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methyithiomethyl (MTM), 2-methoxy-2-propyl (MOP), 2-trinnethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Preparation of (+)-Nalfurafine

The following reaction scheme depicts the synthesis of (+)-nalfurafine:

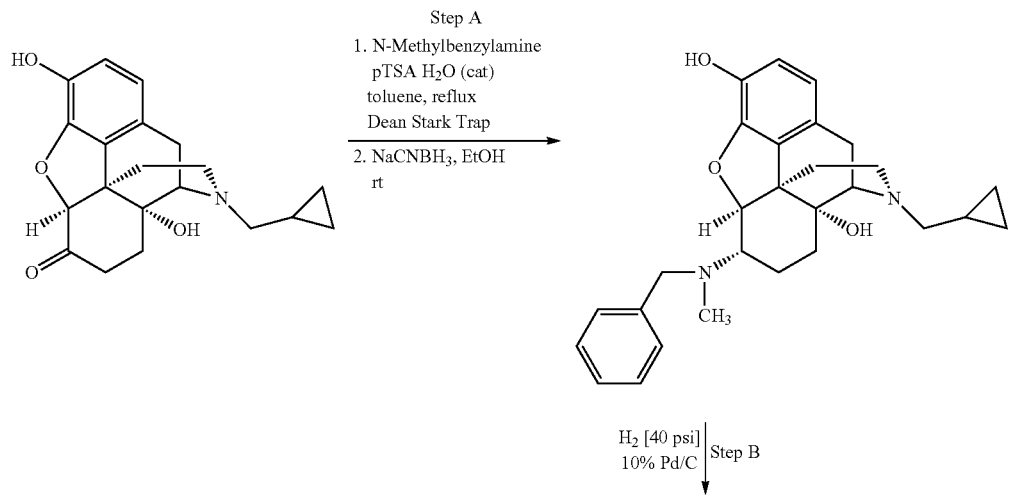

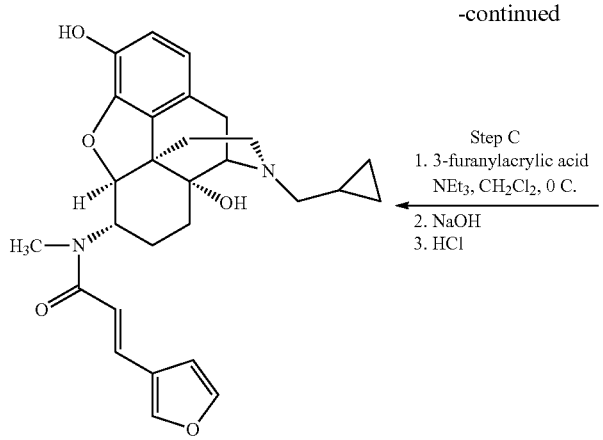
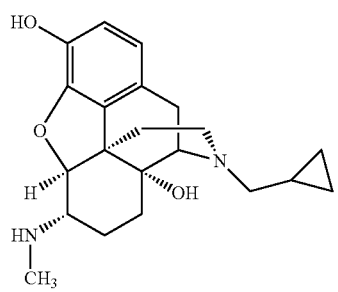

Step A: (+)-Naltrexone (2.0 g, 0.006 moles), N-methylbenzylamine (1.07 g, 0.009 moles), p-toluenesulfonic acid monohydrate (10 mg), and toluene (50 mL) may be introduced into a flask equipped with a Dean Stark Trap. This mixture may be heated to reflux for 12 h over which time water may be removed as an azeotrope. The Dean Stark trap may be exchanged for a short path distillation apparatus. Approximately half the reaction solvent (~25 mL) may be removed through distillation. Upon cooling to room temperature, absolute ethanol (25 mL) may be was introduced followed by $NaCNBH_3$ (390 mg, 0.006 moles). The reaction may be stirred for 6 h at room temperature. Then, distilled water (15 mL) may be added. After stirring for 1 h at room temperature, the mixture may be extracted with ethyl acetate (3×25 mL), the extracts may be combined, dried over anhydrous $MgSO_4$ (~2 g), filtered, and evaporated to dryness. The residue may be chromatographed on $SiO_2$ with 100% EtOAc elution to produce the product (estimated at 1.57 g).

Step B: 6α-N, N-methylbenzyl-(+)-naltrexamine (1.57 g, 0.0035 moles) may be dissolved in glacial acetic acid (20 mL). 10% Pd/C, 50% wet (20 mg) may be added to the Parr bottle containing the reaction mixture. After replacing the atmosphere with hydrogen, the Parr bottle may be pressurized to 40 psi with hydrogen gas. The reaction may be incubated at room temperature for 6 h with shaking (with the hydrogen in the Parr bottle being periodically replaced). After the reaction is deemed complete by HPLC, the contents may be filtered through a celite pad (~1 g of celite), followed by rinsing the pad with glacial acetic acid (5 mL). The filtrate may be cooled to ice-bath temperature, and then neutralized with dropwise addition of 29% $NH_3/H_2O$ to pH 9.3 whereupon a precipitate may be formed. The precipitate may be removed by filtration, washed with distilled water (10 mL), and then dried under vacuum for 24 h, which may produce the product (estimated at 1.2 g).

Step C: To a round bottom flask may be added 3-furanylacrylic acid (0.95 g, 0.007 moles) followed by dichloromethane (10 mL) and 1 drop of dimethylformamide. Oxalyl chloride (1.07 g, 0.008 moles) may be added dropwise. This solution may be warmed to room temperature with stirring and held at that temperature for 2 h. Under reduced pressure, the solvent may be removed until a thick oil (crude 3-furanylacryloyl chloride) remains. Into a separate flask may be added 6α-N-methyl-(+)-naltrexamine (1.2 g, 0.003 moles) and dichloromethane (10 mL). After cooling the solution to ice bath temperature, triethylamine (1.02 g, 0.01 moles) may be added. Then, the previously prepared solution of crude 3-furanylacryloyl chloride in dichloromethane (5 mL) may be added dropwise. The ice bath may be removed and the reaction stirred for 2 h. Distilled water (10 mL) may be added and this mixture stirred for 1 h. The mixture may be transferred into a separatory funnel. The bottom organic layer may be separated and the volatile solvents in the organic layer may be evaporated under reduced pressure to produce a thick oil. To this oil may be added methanol (10 mL) followed by a 10% $NaOH/H_2O$ solution (1.0 mL). This solution may be stirred for 1 hour at room temperature. The pH may be adjusted to 4.2 using glacial acetic acid. Distilled water (5 mL) containing $NaHCO_3$ (2 g) may be added. This mixture may be stirred for 1 hour at room temperature, followed by extraction with chloroform (3×25 mL). The extracts may be combined and dried over anhydrous $MgSO_4$ (1 g). The hydrated $MgSO_4$ may be removed by filtration. The solvents may be removed from the filtrate under reduced pressure affording an oil. The product (1.50 g) may be isolated by column chromatography with 2.5% $MeOH/CHCl_3$ elution.

Example 2

Preparation of (+)-Nalbuphine

The following reaction scheme depicts the synthesis of (+)-nalbuphine:

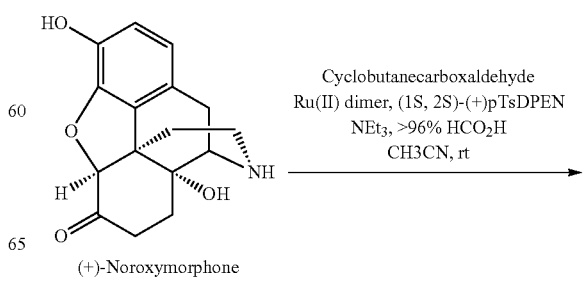

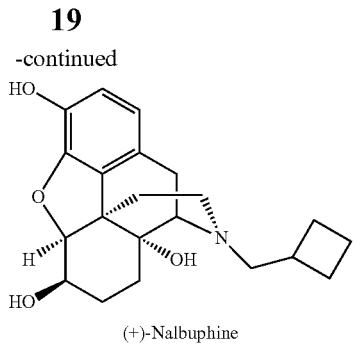

(+)-Nalbuphine

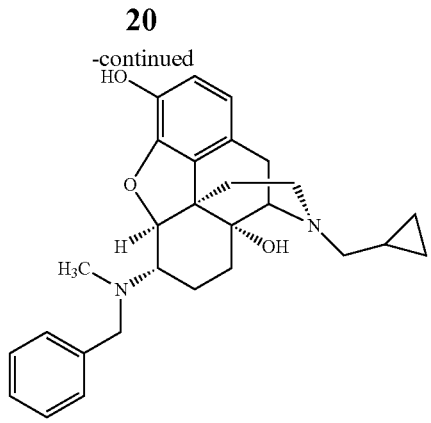

(+)-Noroxymorphone (1.5 g, 0.005 moles) may be dissolved in acetonitrile (10 mL). Cyclobutanecarboxaldehyde (0.88 g, 0.10 moles) may be then added and this reaction stirred at room temperature for 1 h. Then a mixture of triethylamine (2.64 g, 0.026 moles) and >96% formic acid (3.0 g, 0.065 moles) in acetonitrile (10 mL) may be added. Dichloro(p-cymene) Ru(II) dimer (16 mg) and (1S,2S)-(+)-para-toluenesulfonyl-1,2-diphenylethylenediamine (19 mg) may be then added. The reaction may be stirred at room temperature until the reaction is deemed complete by HPLC. Then, the reaction mixture may be evaporated to form a thick oil. Acetonitrile (10 mL) may be added and the reaction stirred at room temperature, wherein a precipitate may form. Filtration of this precipitate, and rinsing with acetonitrile (5 mL), may yield (+)-nalbuphine (estimate at 1.43 g).

Example 3

Preparation of (+)-6β-N-methylnaltrexamine

Step A: (+)-6β-N-benzyl-N-methylnaltrexamine was produced according to the following reaction scheme:

A mixture of (+)-naltrexone (14.9 mmol), N-methylbenzylamine (22.4 mmol), p-toluenesulfonic acid monohydrate (0.147 mmol), and toluene (100 mL) were added to a 3-neck flask equipped with a temperature probe and Dean-Stark apparatus. The mixture was heated to reflux for 16 hours. The reaction was cooled to 35° C., and an anhydrous ethanol solution of sodium cyanoborohydride (14.9 mmol in 75 mL ethanol) was added. The reaction was stirred at room temperature (18-25° C.) for 20 hours. High-performance liquid chromatography indicated the reaction was complete. Distilled water (50 mL) was added and the mixture was stirred for 24 hours. The reaction was filtered. The aqueous layer was extracted with ethyl acetate (2×50 mL). The organic extracts were combined, dried over magnesium sulfate, filtered, and concentrated. The product was isolated in 63% yield following column chromatography and drying under high vacuum for 20 hours.

Step B: (+)-6β-N-methylnaltrexamine was produced according to the following reaction scheme:

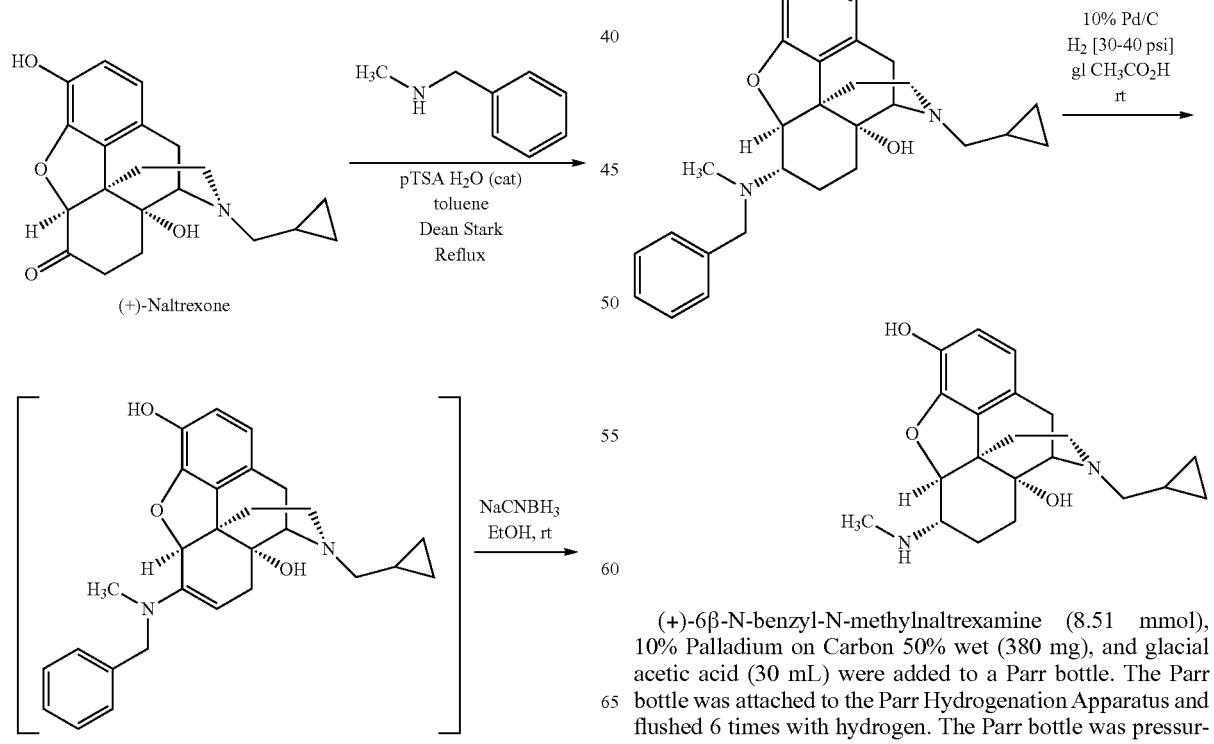

(+)-6β-N-benzyl-N-methylnaltrexamine (8.51 mmol), 10% Palladium on Carbon 50% wet (380 mg), and glacial acetic acid (30 mL) were added to a Parr bottle. The Parr bottle was attached to the Parr Hydrogenation Apparatus and flushed 6 times with hydrogen. The Parr bottle was pressurized to 35 pounds per square inch (psi) and allowed to react for 30 hours at room temperature. High-performance liquid chromatography indicated the reaction was complete. The reaction mixture was filtered through Celite. The filtrate was concentrated, and then distilled water (25 mL) was added. The pH was adjusted to 9.3 with 29% ammonia in water. This mixture was extracted with chloroform (3×25 mL). The organic extracts were combined, dried over magnesium sulfate (3 g), filtered, and concentrated. The product was isolated in 81% yield following column chromatography and drying under high vacuum overnight.

Example 4

Preparation of (+)-6β-N-(2-hydroxyethyl)naltrexamine

Step A: (+)-6β-N-benzyl-N-(2-hydroxyethyl)naltrexamine was produced according to the following reaction scheme:

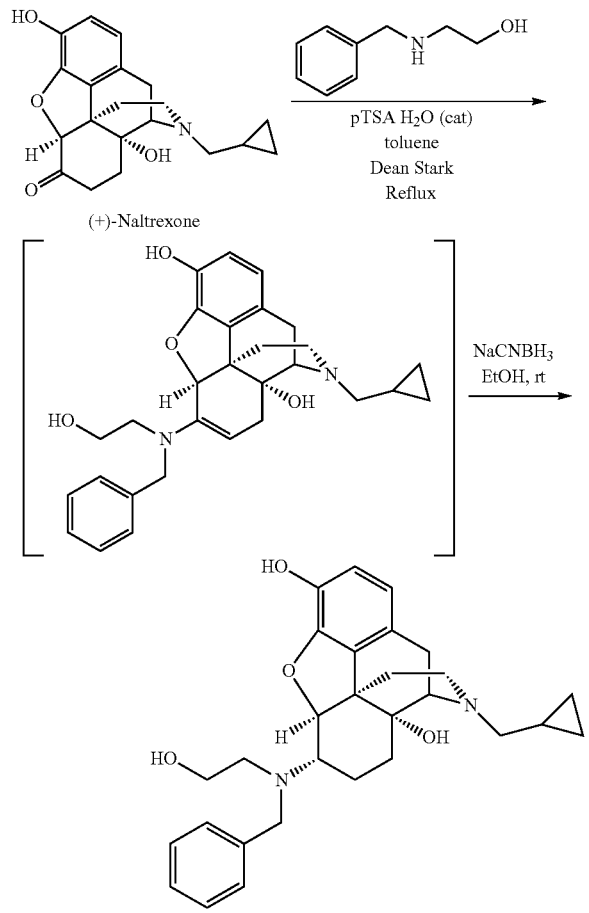

A mixture of (+)-naltrexone (8.44 mmol), N-ethylbenzylethanolamine (12.37 mmol), p-toluenesulfonic acid monohydrate (0.26 mmol), and toluene (200 mL) were added to a 3-neck flask equipped with a temperature probe and Dean-Stark apparatus. The mixture was heated to reflux for 24 hours. The reaction was cooled to 60° C., and an anhydrous ethanol solution of sodium cyanoborohydride (12.7 mmol in 60 mL ethanol) was added. The reaction was stirred at room temperature (18-25° C.) for 20 hours. High-performance liquid chromatography indicated the reaction was complete. Distilled water (60 mL) was added and the mixture was stirred for 2 hours. The aqueous layer was extracted with ethyl acetate (3×50 mL). The organic extracts were combined, dried over magnesium sulfate, filtered, and concentrated. The product was isolated in 50% yield following column chromatography and drying under high vacuum for 48 hours.

Step B: (+)-6β-N-(2-hydroxyethyl)naltrexamine was produced according to the following reaction scheme:

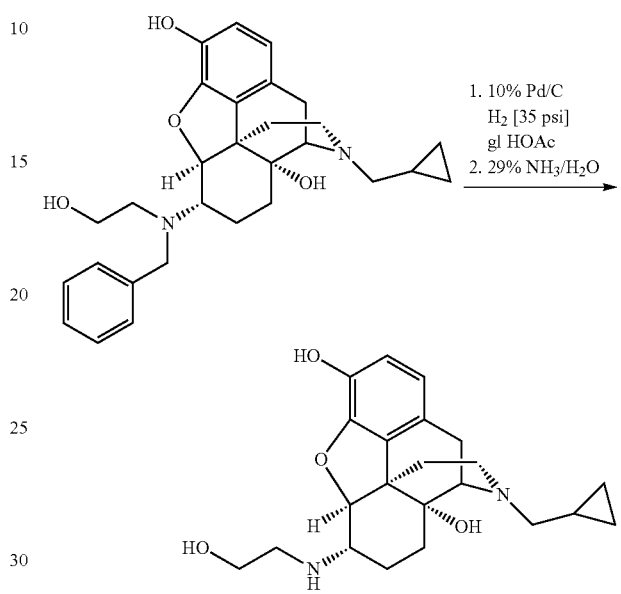

(+)-6β-N-benzyl-N-(2-hydroxyethyl)naltrexamine (3.99 mmol), 10% Palladium on Carbon 50% wet (380 mg), and glacial acetic acid (25 mL) were added to a Parr bottle. The Parr bottle was attached to the Parr Hydrogenation Apparatus and flushed 6 times with hydrogen. The Parr bottle was pressurized to 35 psi and allowed to react for 1 hour at room temperature, then 10 hours at 40° C. High-performance liquid chromatography indicated the reaction was complete. The reaction mixture was filtered through Celite and the Celite was rinsed with glacial acetic acid (10 mL). The filtrate was concentrated, and then distilled water (25 mL) was added. The pH was adjusted to 9.3 with 29% ammonia in water. This mixture was extracted with chloroform (3×20 mL). The organic extracts were combined, dried over magnesium sulfate (3 g), filtered, and concentrated. The product was isolated in 96% yield after drying under high vacuum overnight.

Example 5

Preparation of (+)-6β-N-ethylnaltrexamine

Step A: (+)-6β-N-benzyl-N-ethylnaltrexamine was produced according to the following reaction scheme:

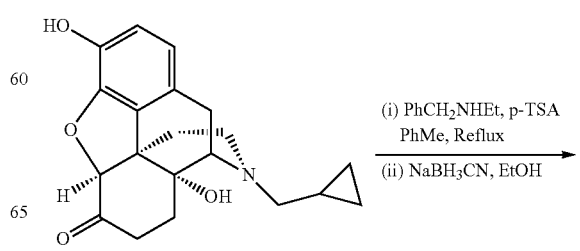

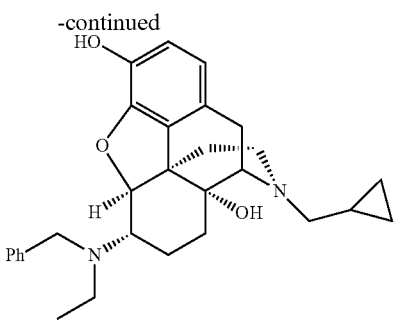

A mixture of (+)-naltrexone (8.00 mmol), N-ethylbenzylamine (16.0 mmol), p-toluenesulfonic acid monohydrate (0.053 mmol), and toluene (130 mL) were added to a 3-neck flask equipped with a temperature probe and Dean-Stark apparatus. The mixture was heated to reflux under nitrogen for 41 hours. The reaction was cooled to 0° C., and anhydrous ethanol (30 mL) and sodium cyanoborohydride (8.75 mmol) were added. The reaction was stirred at room temperature for 19 hours and then at 40° C. under nitrogen for 24 hours. High-performance liquid chromatography indicated the reaction was complete. After cooling to room temperature, distilled water (50 mL) was added and the mixture was stirred for 1 hour. The aqueous layer was extracted with ethyl acetate (2×50 mL). The organic extracts were combined, washed with distilled water (2×75 mL), dried over magnesium sulfate, filtered, and concentrated. The product was isolated by column chromatography in 32% yield.

Step B: (+)-6β-N-ethylnaltrexamine was produced according to the following reaction scheme:

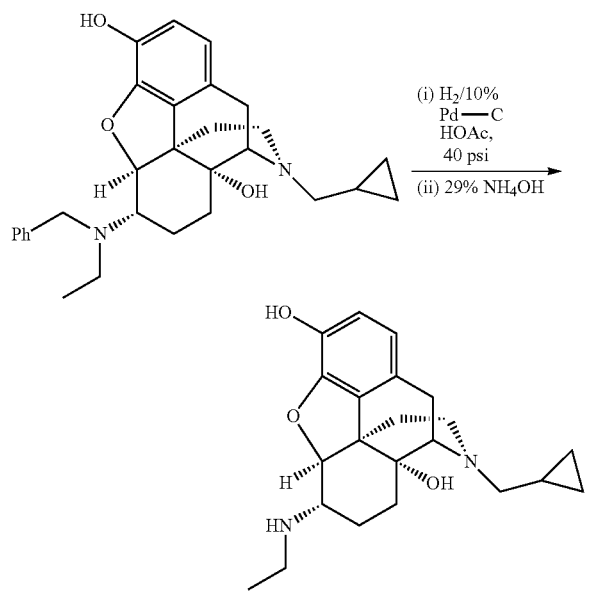

(+)-6β-N-benzyl-N-ethylnaltrexamine (3.47 mmol), 10% Palladium on Carbon 50% wet (320 mg), and glacial acetic acid (16 mL) were added to a Parr bottle. The Parr bottle was attached to the Parr Hydrogenation Apparatus and flushed 6 times with hydrogen. The Parr bottle was pressurized to 40 psi and allowed to react for 4 hours at 40° C., then 2 hours at room temperature. High-performance liquid chromatography indicated the reaction was complete. The reaction mixture was filtered through Celite, and the Celite was washed with glacial acetic acid (5 mL) and distilled water (3×20 mL). The filtrates were combined, and the pH was adjusted to 9.3 with 29% ammonia in water at 0° C. The precipitate was collected by filtration, washed with water (2×10 mL), and dried under high vacuum. The filtrates were extracted with chloroform (2×50 mL). The organic extracts were combined, dried over magnesium sulfate (3 g), filtered, and concentrated. The crude product was filtered through a bed of silica gel and dried under high vacuum to give the product in 90% yield.

Example 6

Preparation of (+)-6β-N-butylnaltrexamine

Step A: (+)-6β-N-benzyl-N-butylnaltrexamine was produced according to the following reaction scheme:

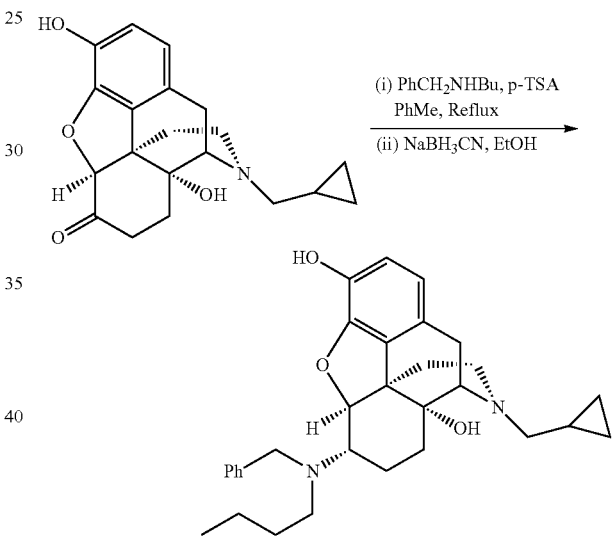

A mixture of (+)-naltrexone (8.00 mmol), N-butylbenzylamine (16.2 mmol), p-toluenesulfonic acid monohydrate (1.20 mmol), and toluene (130 mL) were added to a 3-neck flask equipped with a temperature probe and Dean-Stark apparatus. The mixture was heated to reflux under nitrogen for 24 hours. The reaction was cooled to 0° C., and an anhydrous ethanol solution of sodium cyanoborohydride (12.0 mmol in 30 mL ethanol) was added. The reaction was stirred at 40° C. under nitrogen for 21 hours, then more sodium cyanoborohydride (3 mmol) was added and the reaction continued at 40° C. for another 23 hours. High-performance liquid chromatography indicated the reaction was complete. Distilled water (50 mL) was added and the mixture was stirred for 1 hour at room temperature. The aqueous layer was extracted with ethyl acetate (3×50 mL). The organic extracts were combined, washed with distilled water and brine (2×50 mL), dried over sodium sulfate, filtered, and concentrated. The product was isolated in 35.5% yield by column chromatography.

Step B: (+)-6β-N-butylnaltrexamine was produced according to the following reaction scheme:

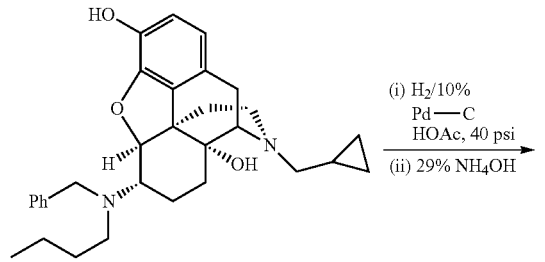

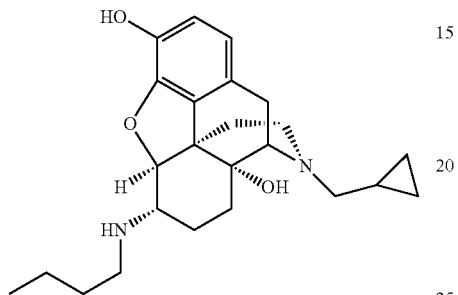

(+)-6β-N-benzyl-N-butylnaltrexamine (3.91 mmol), 10% Palladium on Carbon 50% wet (380 mg), and glacial acetic acid (18 mL) were added to a Parr bottle. The Parr bottle was attached to the Parr Hydrogenation Apparatus and flushed 6 times with hydrogen. The Parr bottle was pressurized to 40 psi and allowed to react for 5 hours at 40° C., then 1 hours at room temperature. High-performance liquid chromatography indicated the reaction was complete. The reaction mixture was filtered through Celite, and the Celite was washed with glacial acetic acid (10 mL) and distilled water (3×20 mL). The filtrates were combined, and the pH was adjusted to 9.3 with 29% ammonia in water at 0° C. The filtrates were saturated with sodium chloride and extracted with chloroform (3×50 mL). The organic extracts were combined, dried over sodium sulfate (3 g), filtered, and concentrated. The crude product was filtered through a bed of silica gel and dried under high vacuum to give the product in 98% yield.

Example 7

Preparation of (4)-6β-N,N-(morpholino)naltrexamine (+)-6β-N,N-(morpholino)naltrexamine was produced according to the following reaction scheme:

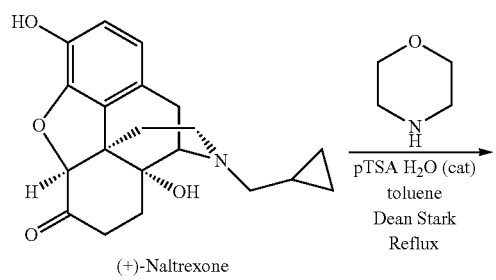

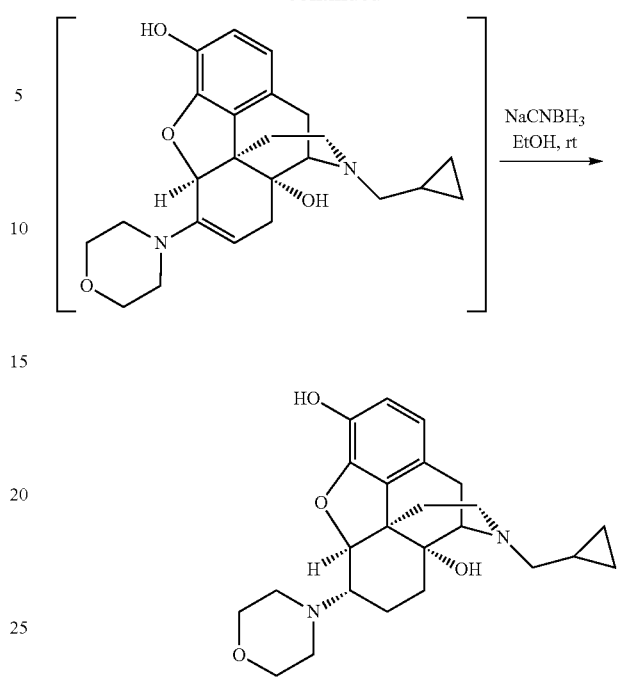

A mixture of (+)-naltrexone (5.86 mmol), morpholine (11.7 mmol), p-toluenesulfonic acid monohydrate (0.26 mmol), and toluene (150 mL) were added to a 3-neck flask equipped with a temperature probe and Dean-Stark apparatus. The mixture was heated to reflux for 24 hours. The reaction was cooled to 40° C., and ethanol (40 mL) and sodium cyanoborohydride (11.7 mmol) were added. The reaction was stirred at room temperature (18-25° C.) for 72 hours. High-performance liquid chromatography indicated the reaction was complete. Distilled water (25 mL) was added and the mixture was stirred for 2 hours. The reaction was extracted with ethyl acetate (3×25 mL). The organic extracts were combined, dried over sodium sulfate, filtered, and concentrated. The product was isolated in 25% yield following column chromatography and drying under high vacuum for 24 hours.

Example 8

Preparation of (+)-6β-N,N-(piperidino)naltrexamine (+)-6β-N,N-(piperidino)naltrexamine was produced according to the following reaction scheme:

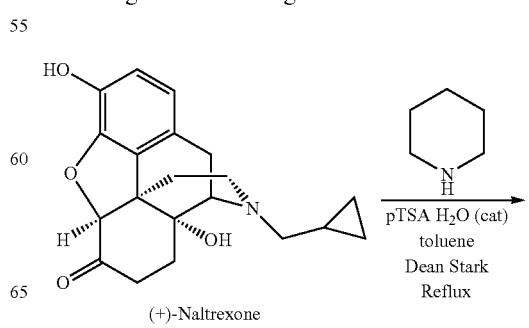

-continued

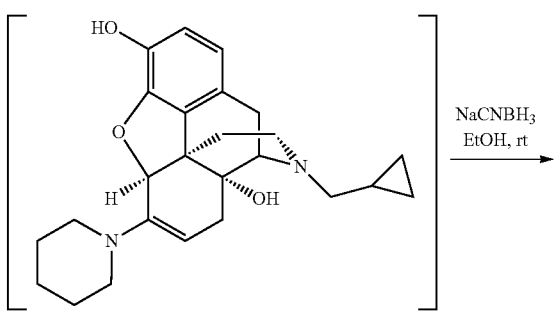

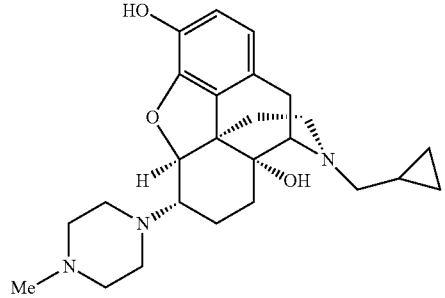

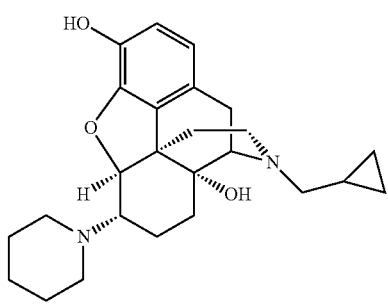

A mixture of (+)-naltrexone (3.95 mmol), piperidine (7.90 mmol), p-toluenesulfonic acid monohydrate (0.53 mmol), and toluene (150 mL) were added to a 3-neck flask equipped with a temperature probe and Dean-Stark apparatus. The mixture was heated to reflux for 24 hours. The reaction was cooled to 50° C., and ethanol (50 mL) and sodium cyanoborohydride (7.90 mmol) were added. The reaction was stirred at room temperature (18-25° C.) for 72 hours. High-performance liquid chromatography indicated the reaction was complete. Distilled water (50 mL) was added and the mixture was stirred for 2 hours. The reaction was extracted with chloroform (3×50 mL). The organic extracts were combined, dried over sodium sulfate, filtered, and concentrated. The product was isolated in 49% yield following column chromatography and drying under high vacuum for 48 hours.

Example 9

Preparation of (+)-6β-N,N-(4-methylpiperazin-1-yl) naltrexamine (+)-6β-N,N-(4-methylpiperazin-1-yl)naltrexamine was produced according to the following reaction scheme:

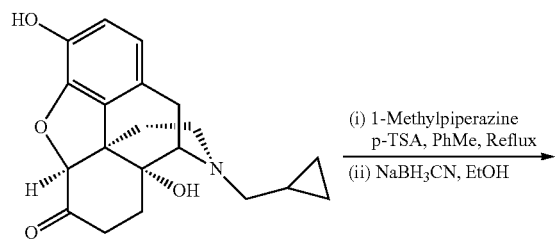

A mixture of (+)-naltrexone (5.57 mmol), 1-methylpiperizine (8.38 mmol), p-toluenesulfonic acid monohydrate (0.60 mmol), and toluene (100 mL) were added to a 3-neck flask equipped with a temperature probe and Dean-Stark apparatus. The mixture was heated to reflux under nitrogen for 17 hours. The reaction was cooled to 0° C., and an anhydrous ethanol solution of sodium cyanoborohydride (8.43 mmol in 5 mL ethanol) was added. The reaction was stirred at room temperature (18-25° C.) under nitrogen for 6 hours. High-performance liquid chromatography indicated the reaction was complete. Distilled water (50 mL) was added and the mixture was stirred for 1 hour. The reaction was extracted with ethyl acetate (2×50 mL). The organic extracts were combined, washed with distilled water (2×50 mL) and brine (50 mL), dried over sodium sulfate, filtered, and concentrated. The product was isolated by column chromatography and recrystallization in 52% yield.

Example 10

Preparation of (+)-6β-N,N-dipropylnaltrexamine (+)-6β-N,N-dipropylnaltrexamine was produced according to the following reaction scheme:

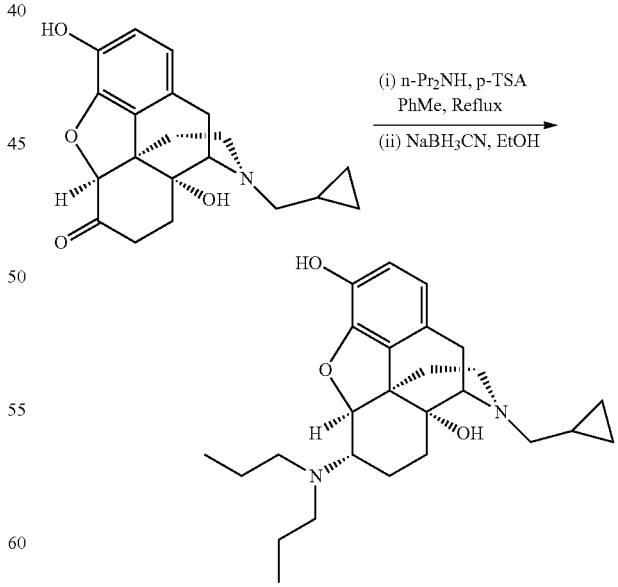

A mixture of (+)-naltrexone (5.00 mmol), dipropylamine (8.38 mmol), p-toluenesulfonic acid monohydrate (0.095 mmol), and toluene (100 mL) were added to a 3-neck flask equipped with a temperature probe and Dean-Stark apparatus. The mixture was heated to reflux under nitrogen for 20 hours. The reaction was cooled to 0° C., and an anhydrous ethanol solution of sodium cyanoborohydride (7.48 mmol in 5 mL ethanol) was added. The reaction was stirred at room temperature (18-25° C.) under nitrogen for 6 hours. High-performance liquid chromatography indicated the reaction was complete. Distilled water (50 mL) was added and the mixture was stirred for 1 hour. The reaction was extracted with ethyl acetate (2×50 mL). The organic extracts were combined, washed with distilled water (2×50 mL) and brine (50 mL), dried over sodium sulfate, filtered, and concentrated. The product was isolated by column chromatography in 16.4% yield.

Example 11

Preparation of (+)-6β-N,N-dibenzylnaltrexamine (+)-6β-N,N-dibenzylnaltrexamine was produced according to the following reaction scheme:

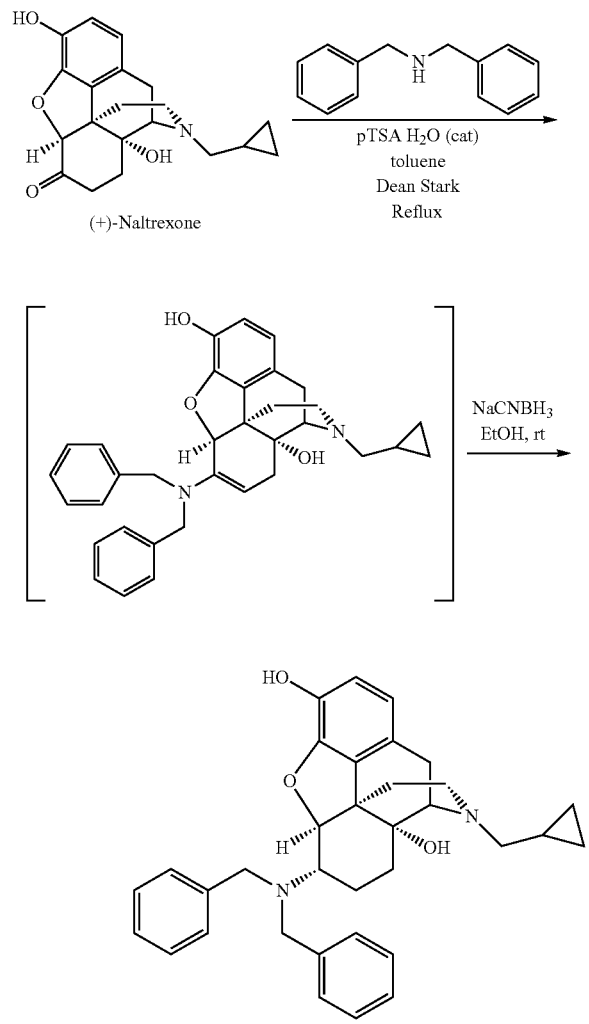

A mixture of (+)-naltrexone (14.35 mmol), dibenzylamine (28.7 mmol), p-toluenesulfonic acid monohydrate (0.53 mmol), and toluene (200 mL) were added to a 3-neck flask equipped with a temperature probe and Dean-Stark apparatus. The mixture was heated to reflux under nitrogen for 48 hours. The reaction was cooled to 40° C., and sodium cyanoborohydride (21.5 mmol) and ethanol (75 mL) were added. The reaction was stirred at 40° C. for 48 hours. High-performance liquid chromatography indicated the reaction was complete. Dilute HCl (10% in water, 50 mL) was added and the mixture was stirred for 2 hours. The pH was adjusted to 9.2 with 29% ammonia in water. The reaction mixture was extracted with ethyl acetate (3×50 mL). The organic extracts were combined, dried over magnesium sulfate, filtered, and concentrated. The product was isolated in 29% yield following column chromatography and drying under high vacuum for 20 hours.

Example 12

Debenzylation of (+)-6β-N,N-dibenzylnaltrexamine to give (+)-6β-naltrexamine (+)-6β-naltrexamine was produced according to the following reaction scheme:

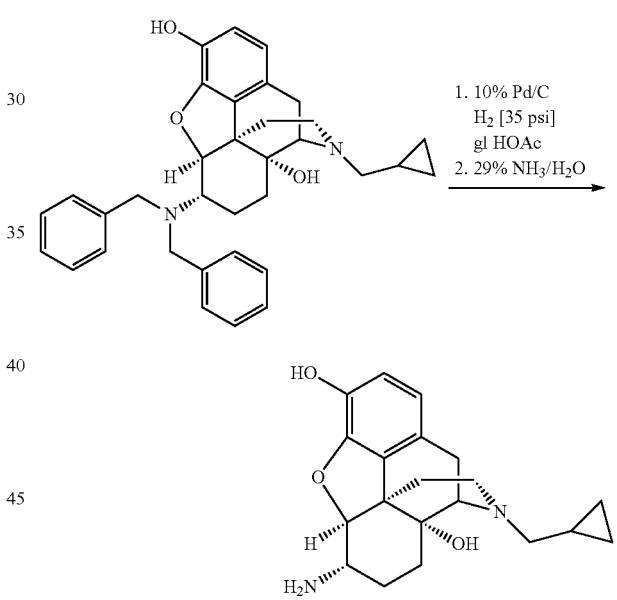

(+)-6β-N,N-dibenzylnaltrexamine (5.36 mmol), 10% Palladium on Carbon 50% wet (280 mg), and glacial acetic acid (15 mL) were added to a Parr bottle. The Parr bottle was attached to the Parr Hydrogenation Apparatus and flushed 6 times with hydrogen. The Parr bottle was pressurized to 35 psi and allowed to react for 1 hour at room temperature, then for 6 hours at 50° C. High-performance liquid chromatography indicated the reaction was complete. The reaction mixture was filtered through Celite, and the Celite was washed with glacial acetic acid (15 mL). The filtrates were combined, concentrated, and the pH was adjusted to 9.4 with 29% ammonia in water. The filtrates were extracted with chloroform (3×50 mL). The organic extracts were combined, dried over sodium sulfate, filtered, and concentrated. The product was dried under high vacuum overnight.

Example 13

Preparation of (+)-6β-N,N-di(2-hydroxyethyl)naltrexamine (+)-6β-N,N-di(2-hydroxyethyl)naltrexamine was produced according to the following reaction scheme:

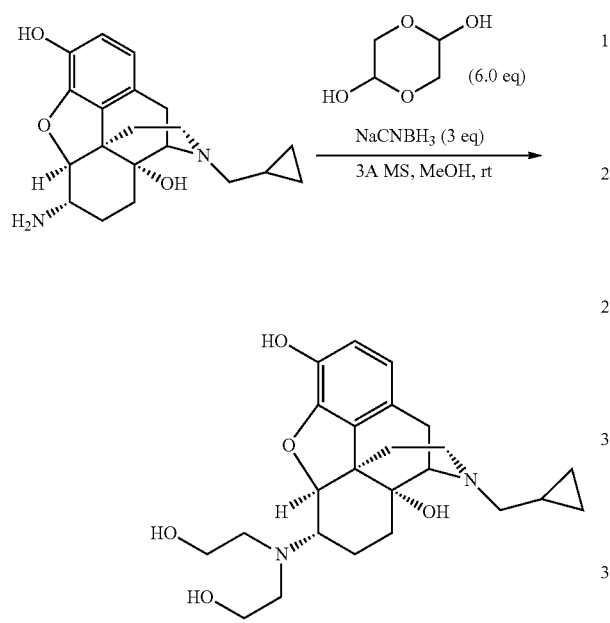

The crude (+)-6β-naltrexamine (assume 100% conversion, 5.34 mmol) was dissolved in anhydrous methanol (20 mL). To this solution was added glycolaldehyde dimer (32 mmol), 3 Å Molecular Sieves (2.5 g), and sodium cyanoborohydride (16.02 mmol). The reaction was stirred at room temperature overnight. High-performance liquid chromatography indicated the reaction was complete. The reaction mixture was filtered and concentrated, and the pH was adjusted to 9.2 with 29% ammonia in water. The mixture was extracted with chloroform (3×25 mL). The organic extracts were combined, dried over magnesium sulfate, filtered, and concentrated. The product was isolated in 75% yield (over two steps) following column chromatography and drying under high vacuum for 24 hours.

What is claimed is:

1. A process for preparing a (+)-morphinan compound of Formula (IV), the process comprising:

(a) contacting a compound of Formula (III) with a secondary amine of formula $NHR^8R^9$ and an acid catalyst to form an intermediate enamine compound; and (b) contacting the intermediate enamine compound with an alkali metal cyanoborohydride to form the compound of Formula (IV) according to the following reaction scheme:

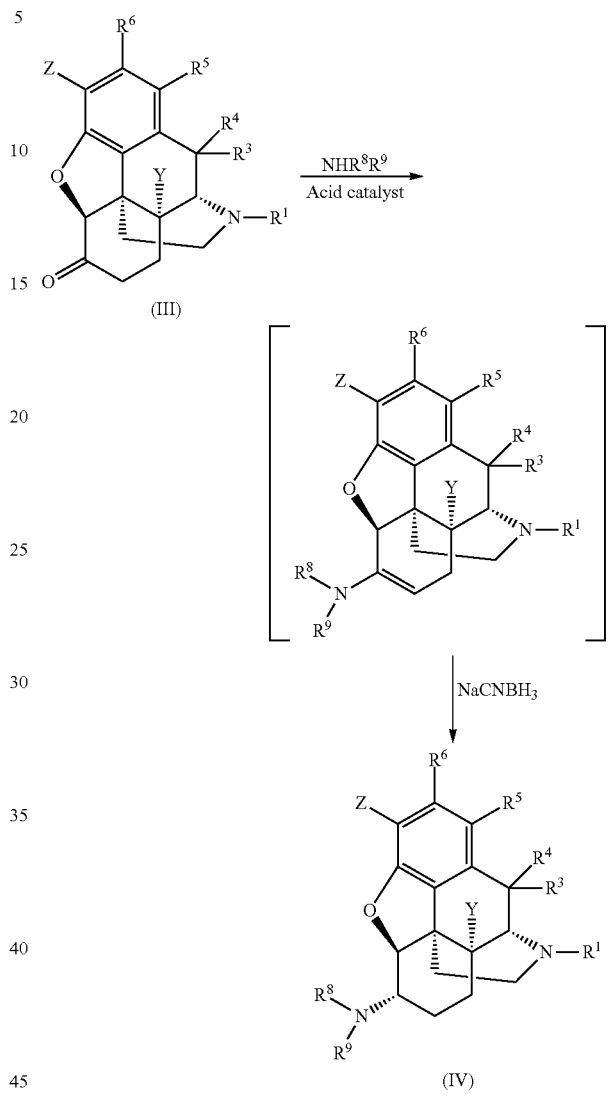

wherein:
$R^1$ is chosen from hydrocarbyl and substituted hydrocarbyl;
$R^3$ and $R^4$ are independently chosen from hydrogen, hydrocarbyl, and substituted hydrocarbyl;
$R^5$ and $R^6$ are independently chosen from hydrogen, hydrocarbyl, substituted hydrocarbyl, halogen, {—}OH, {—}NH$_2$, and {—}OR$^7$;
$R^7$ is chosen from hydrocarbyl and substituted hydrocarbyl;
$R^8$ and $R^9$ are independently chosen from acyl, acyloxy, alkyl, cycloalkyl, alkoxy, hydroxy alkyl, alkenyl, aryl, aryloxy, substituted alkyl, substituted cycloalkyl, substituted alkenyl, substituted aryl, and together $R^8$ and $R^9$ form a ring or ring system chosen from carbocyclic, substituted carbocyclic, heterocyclic, substituted heterocylic, and a combination thereof;
provided that when one of $R^8$ or $R^9$ is benzyl, then the other of $R^8$ or $R^9$ is other than $C_1$-$C_6$ alkyl or $C_6$-$C_{12}$ aryl;
Y is chosen from hydrogen, hydroxy, protected hydroxy, alkoxy, and acyloxy; and Z is chosen from hydroxy, protected hydroxy, alkoxy, and acyloxy.

2. The process of claim 1, wherein $R^1$ is chosen from alkyl, cycloalkyl, cycloalkylmethyl, alkenyl, alkynyl, and aryl.

3. The process of claim 1, wherein $R^3$, $R^4$, $R^5$, and $R^6$ are hydrogen.

4. The process of claim 1, wherein the mole to mole ratio of the compound of Formula (III) to the secondary amine of formula $NHR^8R^9$ is from about 1:1 to about 1:3.

5. The process of claim 1, wherein the acid catalyst is a sulfonic acid chosen from p-toluenesulfonic acid, methanesulfonic acid, ethanedisulfonic acid, benzenesulfonic acid, and trifluromethanesulfonic acid.

6. The process of claim 1, wherein the mole to mole ratio of the compound of Formula (III) to the acid catalyst is from about 1:0.005 to about 1:0.2.

7. The process of claim 1, wherein step (a) is conducted in the presence of a solvent or solvent system comprising benzene, n-butanol, butyl acetate, carbon tetrachloride, chloroform cyclohexane, 1,2-dichloroethane, dichloromethane, ethyl acetate, di-ethyl ether, heptane, hexane, methyl-1-butyl ether, methyl ethyl ketone, pentane, di-isopropyl ether, toluene, trichloromethane, xylene, or a combination thereof.

8. The process of claim 1, wherein the mole to mole ratio of the compound of Formula (III) to the alkali metal cyanoborohydride is from about 1:0.5 to about 1:3.

9. The process of claim 1, wherein step (a) is conducted at a temperature of about 30° C. to about 130° C., and step (b) is conducted at a temperature of about 10° C. to about 100° C.

10. The process of claim 1, wherein the carbons at positions 5, 13, 14, and 9 of the compounds of Formula (III) or (IV) have S, R, R, and S configurations, respectively.

11. The process of claim 1, wherein the carbon at position 6 of the compound of Formula (IV) has a beta configuration.

12. The process of claim 1, wherein the compound of Formula (IV) is converted to a pharmaceutically acceptable salt.

13. The process of claim 1, wherein $R^1$ is chosen from methyl, cyclopropylmethyl, cyclobutylmethyl, allyl, propargyl, and benzyl; $R^3$, $R^4$, $R^5$, and $R^6$ are hydrogen.

14. The process of claim 13, wherein the mole to mole ratio of the compound of Formula (III) to the secondary amine of formula $NHR^8R^9$ is from about 1:1.5 to about 1:2.

15. The process of claim 13, wherein the acid catalyst is p-toluenesulfonic acid and the mole to mole ratio of the compound of Formula (III) to the acid catalyst is from about 1:0.01 to about 1:0.15.

16. The process of claim 13, wherein step (a) is conducted in the presence of a solvent or solvent system comprising toluene, and step (a) is conducted at a temperature of about 110° C. to about 115° C.

17. The process of claim 13, wherein the alkali metal cyanoborohydride is sodium cyanoborohydride; the mole to mole ratio of the compound of Formula (III) to sodium cyanoborohydride is from about 1:1 to about 1:2, and step (b) is conducted at temperature of about 20° C. to about 80° C.

18. The process of claim 13, wherein the carbons at positions 5, 13, 14, and 9 of the compounds of Formula (III) or (IV) have S, R, R, and S configurations, respectively.

19. The process of claim 13, wherein the carbon at position 6 of the compound of Formula (IV) has a beta configuration.

20. The process of claim 13, wherein the compound of Formula (IV) is converted to a pharmaceutically acceptable salt.

* * * * *